(12) United States Patent
Lamont et al.

(10) Patent No.: US 6,200,564 B1
(45) Date of Patent: Mar. 13, 2001

(54) PHARMACEUTICAL COMPOSITIONS CONTAINING CHONDROITINASE AND USES THEREFOR

(76) Inventors: J. Thomas Lamont, 390 Waltham St., Newton, MA (US) 02465; K. Ramakrishnan Bhaskar, 95 Burlington St., Lexington, MA (US) 02420; Allan M. Green, 19 Francis Ave., Cambridge, MA (US) 02138

( * ) Notice: Subject to any disclaimer, the term of this patent is extended or adjusted under 35 U.S.C. 154(b) by 0 days.

(21) Appl. No.: 09/058,684

(22) Filed: Apr. 10, 1998

Related U.S. Application Data

(60) Provisional application No. 60/043,898, filed on Apr. 11, 1997.

(51) Int. Cl.[7] .................................................... A61K 38/47

(52) U.S. Cl. ................... 424/94.61; 424/94.1; 424/94.6; 514/851

(58) Field of Search ................................. 424/94.1, 94.6, 424/94.61; 514/851

(56) References Cited

U.S. PATENT DOCUMENTS

| | | | |
|---|---|---|---|
| 3,502,779 | * | 3/1970 | Dye et al. ............................. 514/706 |
| 4,636,195 | * | 1/1987 | Wolinsky .............................. 604/509 |
| 5,112,758 | | 5/1992 | Fellman et al. ......................... 436/8 |
| 5,932,481 | * | 8/1999 | Pon et al. .............................. 436/87 |

FOREIGN PATENT DOCUMENTS

| | | |
|---|---|---|
| 205 332 | 12/1983 | (DE) . |
| 0 285 439 | 10/1988 | (EP) . |
| 0 613 949 | 2/1994 | (EP) . |
| 742792 | 6/1980 | (SU) . |
| WO 90/06954 | 6/1990 | (WO) . |
| WO 95/29256 | 11/1995 | (WO) . |
| WO 96/30051 | 10/1996 | (WO) . |
| WO 97/193351 | 5/1997 | (WO) . |

OTHER PUBLICATIONS

Bhaskar et al. Am. Rev. Resp. Dis. vol. 143 (3) pp. 640–648, abstract enclosed, 1991.*
Hill et al. Biochem. Mol. Med. vol. 62 (1), pp. 85–94, abstract enclosed, 1997.*
Brahimihorn et al. Europ. J. Cell Biol. vol. 64(2), pp. 271–280, abstract enclosed, 1994.*
Bataillon et al. J. Antimicrob. Chemother. vol. 29(5), pp. 499–508, abstract enclosed, 1992.*
Berkow et al., "The Merck Manual", Merck Res, p. 599. (1992);.
Rahmoune et al., "Chondroitin sulfate in sputum from cystic fibrosis and chronic bronchitis" Am. J. Cell. Mol. Biol., vol. 5, pp. 315–320 (1991).

Bartolucci, C. et al. "Chondroprotective Action of Chondroitin Sulfate. Competitive Action of Chondroitin Sulfate on hte Digestion of Hyaluronan by Bovine Testicular Hyaluronidase" *Int. J. Tiss. Reac.* XIII(6):311–317 (1991);.

Bhaskar, K.R. et al. "Dysregulation of Proteoglycan Production by Intrahepatic Biliary Epithelial Cells bearing Defective (Delta–f508) Cystic Fibrosis Transmembrane Conductance Regulator" *Hepatology* 27(1):7–14 (1998);.

Fibbi, G. et al. "Involvement of Chondroitin Sulphate in Preventing Adhesive Cellular Interactions" *Biochimica et Biophysica Acta* 762:512–518 (1983).

Hayashi, S. et al. "Contribution of β–Glucuronidase to the Degradation of Chondroitin 4–Sulfate by Canine Liver Lysosomal Enzymes" *Tohoku J. Exp. Med.* 127:317–326 (1979);.

Hayashi, S. "Study on the Degradation of Glycosaminoglycans by Canine Liver Lysosomal Enzymes" *J. Biochem.* 83:149–157 (1978);.

Knudson, W. "Selective Hydrolysis of Chondroitin Sulfates by Hyaluronidase" *Biochemistry* 23:368–375 (1984);.

Liau, Y.H. et al. "Degradation of Chondroitin 4–Sulfate by Rat Stomach Exoglycosidases, Sulfohydrolase and Hyaluronidase–Like Enzymes" *Digestion* 21:117–124 (1981);.

Liau, Y.H. et al. "Heterogeneity of Rat Rib Chondroitin Sulfate and Susceptibility to Rat Gastric Chondrosulfatase" *Biochimica et Biophysica Acta* 539:315–323 (1978);.

Smedsrød, et al. "Endocytosis and Degradation of Chondroitin Sulphate by Liver Endothelial Cells" *Biochem. J.* 229:63–71 (1985).

* cited by examiner

*Primary Examiner*—Christopher Tate
(74) *Attorney, Agent, or Firm*—Lahive & Cockfield, LLP

(57) ABSTRACT

Gastrointestinal mucus from patients suffering from cystic fibrosis has been found to contain large amounts of chondroitin sulfate polymer. This finding indicates that the enzyme chondroitinase is useful for preventing gastrointestinal mucus from accumulating in cystic fibrosis patients, and subjects suffering from other diseases or conditions characterized by excess mucus secretion.

6 Claims, 10 Drawing Sheets

Overnight culture with 3H GlcN

Overnight culture with 3H GlcN

PHARMACEUTICAL COMPOSITIONS CONTAINING CHONDROITINASE AND USES THEREFOR

RELATED APPLICATION

This application claims priority to the U.S. Provisional Application Ser. No. 60/043,898 entitled "Pharmaceutical Compositions Containing Chondroitinase and Uses Therefor," filed Apr. 11, 1997, the teachings of which are incorporated herein by reference.

BACKGROUND OF THE INVENTION

Cystic fibrosis (CF) is a common lethal genetic disorder affecting approximately 1 in 2000 Caucasians[1]. The major pathological manifestations in CF are obstruction of pulmonary, gastrointestinal and pancreatobiliary ducts by accumulation of mucoid secretions ultimately leading to organ failure, particularly in the lung. The basic cellular defect in CF is abnormal chloride transport due to mutation of the cystic fibrosis transmembrane conductance regulator (CFTR) gene[2-7]. The CFTR gene encodes a protein required for the normal function of a cAMP regulated chloride channel present in secretory and other cells throughout the body. Despite rapid advances in our knowledge of the structure and function of CFTR, the cellular and physiological basis of the mucus abnormalities in CF remain obscure.

Liver disease is the second leading cause of death in CF, after lung disease [8,9]. The major hepatic manifestation of CF is a distinct form of focal biliary cirrhosis, a condition that may be accompanied or preceded by inspissated cosinophilic material resembling the mucoid material found in other organs of CF patients[10]. Approximately 20% of surviving adolescents and adults with CF have morphologic evidence of liver disease, and about 10 to 15% of these develop complications of fibrosis, cirrhosis and portal hypertension requiring transplantation[11]. Other manifestations of biliary tract disease in CF include biliary sludge and casts, increased incidence of gallstones and common bile duct strictures. Very little is known of the pathogenesis of hepatobiliary disease in CF, and detailed analysis of the inspissated material plugging bile ductules has not been published. The abnormalities in biliary secretion are assumed to be related to the known single gene defect in CF, mutation of the CFTR. Recent studies by Cohen et al[12] have documented that CFTR is localized in liver exclusively to the apical membrane of bile duct cells, but not in hepatocytes. This suggests that the hepatobiliary abnormalities in CF, particularly focal biliary cirrhosis, originate in bile duct cells, possibly by dysregulation of glycoprotein synthesis.

The availability of immortalized human intrahepatic biliary epithelial cells from normal and CF patients allow direct comparison of synthesis and secretion of biliary macromolecules in vitro.

SUMMARY OF THE INVENTION

This invention is based, at least in part, on the discovery that the major glucoconjugate secreted by IBE cells is chondroitin sulfate and more significantly that the secretion of this proteoglycan is dysregulated in CF-IBE cells compared to cells with normally functioning CFTR.

The present invention pertains to methods for treating subjects having disorders characterized by the obstruction of pulmonary, gastrointestinal and pancreatobiliary ducts by the accumulation of mucoid secretions. For example, the invention pertains to methods for treating a subject having a disorder characterized by the obstruction of organ ducts by the accumulation of mucoid secretions, e.g., a pulmonary disorder, e.g., lung failure occurring in patients afflicted with, e.g., cystic fibrosis. These methods include administering to the subject an agent capable of preventing chondroitin sulfate accumulation such that treatment of the subject occurs.

In a preferred embodiment, the agent is capable of preventing chondroitin sulfate accumulation by degrading chondroitin sulfate. In another preferred embodiment, the agent is capable of preventing chondroitin sulfate accumulation by inhibiting the production of chondroitin sulfate.

In another embodiment, the invention pertains to methods for treating a subject having a pancreatobiliary disorder, e.g., biliary cirrhosis, biliary sludge, gallstones, and common bile duct strictures comprising administering to the subject an agent capable of preventing chondroitin sulfate accumulation such that treatment occurs.

In a preferred embodiment, the agent capable of preventing chondroitin sulfate accumulation is an enzyme, e.g., chondroitinase enzyme. In still another embodiment, the agent capable of degrading chondroitin sulfate, e.g., an enzyme, e.g., chondroitinase enzyme, is produced in recombinant expression vector and host cell for use in gene therapy for treating a subject.

The invention also pertains to methods for detecting or diagnosing a disorder characterized by the obstruction of pulmonary, or pancreatobiliary ducts by the accumulation of mucoid secretions, e.g., cystic fibrosis. In one embodiment, the method involves contacting a cell, tissue, or fluid sample, e.g., a sputum sample, from the subject with an agent, e.g. $^3$H-glucosamine, capable of detecting a glycosaminoglycan (GAG), e.g., chondroitin sulfate, determining the amount of chondroitin sulfate expressed in the sample, comparing the amount of chondroitin sulfate expressed in the sample to a control sample and forming a diagnosis based on the amount of chondroitin sulfate expressed in the sample as compared to the control sample. Kits for detecting chondroitin sulfate in a biological sample are also within the scope of the invention.

The invention also pertains to methods for monitoring a previously diagnosed subject with a disease characterized by the obstruction of pulmonary or pancreatobiliary ducts by the accumulation of mucoid secretions, e.g., pulmonary, gastrointestinal, or pancreatobiliary disorders, e.g., lung failure, biliary cirrhosis, biliary sludge, gallstones, or common bile strictures in a biological sample. These methods involve contacting a cell, tissue, or fluid sample, e.g., a sputum sample, from the subject with an agent, e.g., $^3$H-glucosamine, capable of detecting a glycosaminoglycan (GAG), e.g., chondroitin sulfate, determining the amount of chondroitin sulfate expressed in the sample, comparing the amount of chondroitin sulfate expressed in the sample to a the amount of chondroitin sulfate expressed in a sample previously obtained from the same subject to determine the progression of the disease, e.g., measuring the increase or decrease in levels of a GAG, e.g., chondroitin sulfate over time in a subject.

Still another aspect of the invention pertains to methods, e.g., screening assays, for identifying a compound for treating a disorder characterized by the obstruction of pulmonary, gastrointestinal and pancreatobiliary ducts by the accumulation of mucoid secretions, e.g., cystic fibrosis. These methods typically include assaying the ability of the compound or agent to prevent accumulation of a GAG, e.g., chondroitin sulfate, thereby identifying a compound for treating a disorder characterized by the obstruction of pulmonary, gastrointestinal and pancreatobiliary ducts by the accumulation of mucoid secretions, e.g., cystic fibrosis. In a preferred embodiment, the method involves contacting a biological sample obtained from a subject having the disorder with the compound or agent, determining the amount of GAG, e.g., chondroitin sulfate, expressed in the biological sample, comparing the amount of chondroitin sulfate expressed in the biological sample to that of a control sample. An alteration in the amount of chondroitin sulfate expressed in the sample exposed to the compound or agent in comparison to the control is indicative of modulating the degradation of chondroitin sulfate.

Cells were plated at the same density in six-well plates and after overnight culture in the presence of radioactive precursor, medium and cell homogenates were analyzed. Values for all six individual wells of each cell line are shown to demonstrate reproducibility.

Figure 7A:
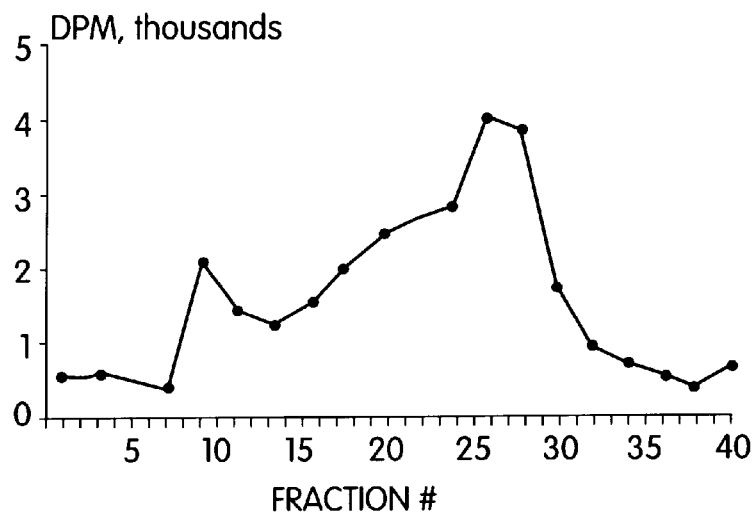
Figure 7B:
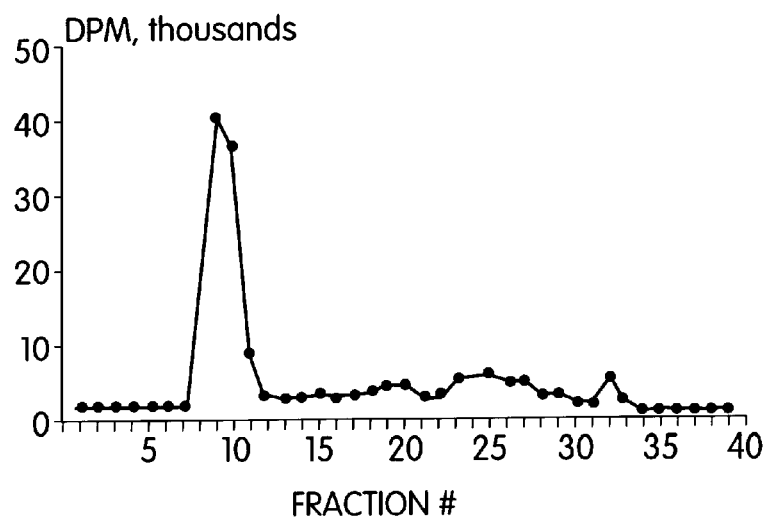

FIG. 7. Gel filtration patterns of medium from normal (left) and CF (right) IBE cells. Radioactive precursor incorporation is exclusively in large macromolecules (fractions with #12 and below) in the case of CF cells whereas in the case of normal cells, there is considerable incorporation of radioactivity in smaller glycoconjugates (fraction #s 15–30). Note also the ten-fold higher counts of radioactivity in medium from the CF cells.

Figure 8A:
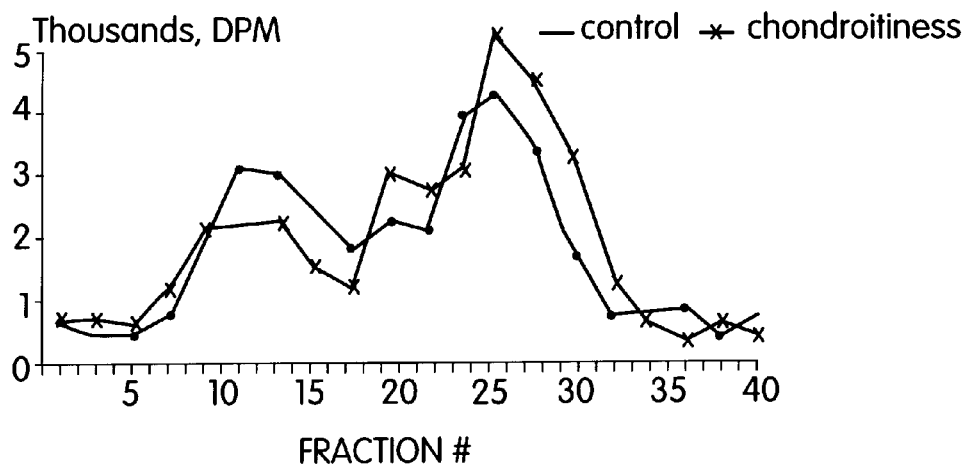
Figure 8B:
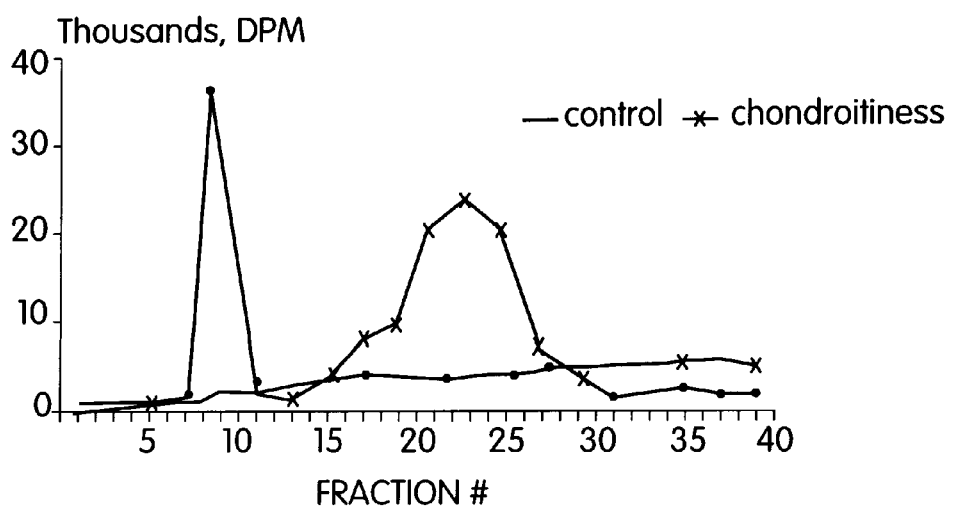

FIG. 8. Effect of chondroitinase treatment on medium from normal (left) and CF (right) IBE cells.

Radiolabel in CF-cell medium, which is exclusively in fractions 8–12 (large macromolecules) before digestion is entirely shifted to fractions 15–30 (smaller size) after enzyme treatment indicating chondroitin sulfate is the predominant glycoconjugate secreted. Digestion of medium from normal cell is only partial suggesting the secreted glycoconjugate includes other types besides chondroitin sulfate.

Figure 9A:
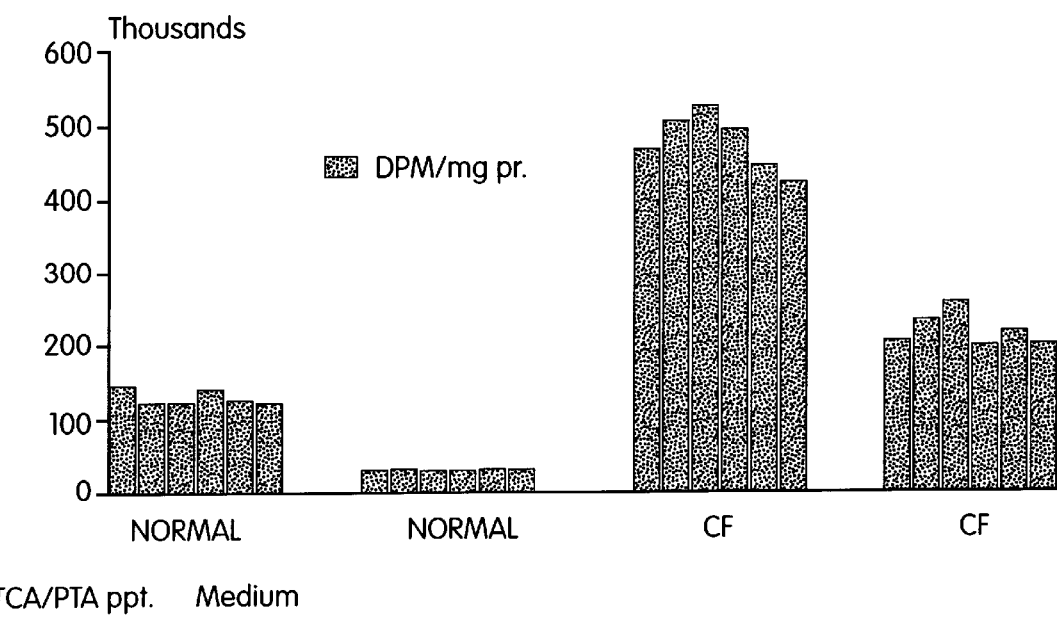
Figure 9B:
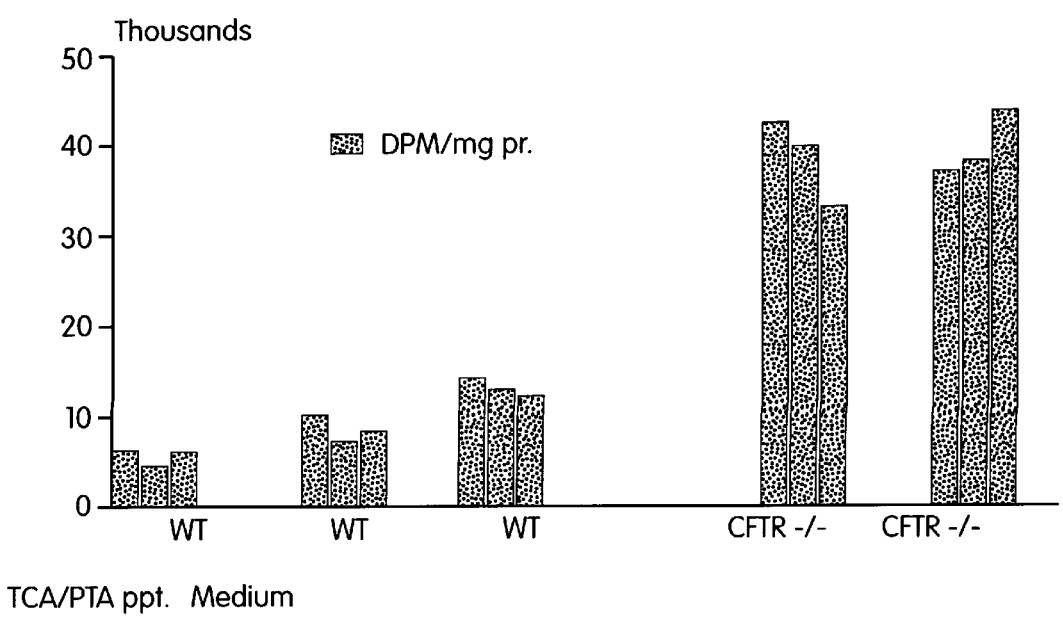

FIG. 9. A marked increase in radioactive glucosamine incorporation is also seen in tissue culture of intestine from knockout mice without functioning CFTR (CFTR −/−) compared to wild type (WT) mice. Results of medium from IBE cells are included for ease of comparison.

DETAILED DESCRIPTION OF THE INVENTION

Hepatic dysfunction in cystic fibrosis (CF) has been attributed to accumulation of viscous mucoid secretions in intrahepatic bile ducts. The purpose of our study was to compare glycoconjugate secretion by intrahepatic biliary epithelial (IBE) cells derived from normal livers and livers of CF patients with the delta F508 mutation of the cystic fibrosis transmembrane conductance regulator. Confluent cells were incubated with $^3$H-glucosamine for 16 h and radiolabeled macromolecules were analyzed for amount and type of glycoconjugates. Incorporation of $^3$H-glucosamine into macromolecular glycoconjugates was 2–3 fold higher in CF cells vs. normals. Gel exclusion chromatography on Sepharose C1 4B revealed that the secreted glycoconjugates from CF cells eluted entirely in the excluded fraction (mol. w>$2\times10^6$) while the in the normal cells approximately 60% of radiolabel was in lower molecular weight species. These high molecular weight glycoconjugates in both CF and normal cells were identified as chondroitin sulfates as evidenced by susceptibility to beta elimination, chondroitinase ABC digestion and amino acid composition. Western blotting of IBE cell secretions with a polyclonal antibody to chondroitin sulfate revealed proteoglycan bands at 100 and 210 kd. Our results indicate that chondroitin sulfate is the major $^3$H-glucosamine labeled glycoconjugate secreted by IBE cells in vitro and IBE cells from CF patients secrete more chondroitin sulfate than normals. Since chondroitin sulfate might increase the aggregation of viscous properties of glycoconjugates in epithelial secretions, oversecretion and accumulation of this proteoglycan in CF patients could promote small bile duct obstruction.

Gastrointestinal mucus from patients suffering from cystic fibrosis has been found to contain large amounts of chondroitin sulfate polymer. This finding indicates that the enzyme chondroitinase is useful for dissolving gastrointestinal mucus in cystic fibrosis patients, and subjects suffering from other diseases or conditions characterized by excess mucus secretion.

This invention is based, at least in part, on the discovery that the major glucoconjugate secreted by IBE cells is chondroitin sulfate and more significantly that the secretion of this proteoglycan is dysregulated in CF-IBE cells compared to cells with normally functioning CFTR.

The present invention pertains to methods for treating subjects having disorders characterized by the obstruction of pulmonary, gastrointestinal and pancreatobiliary ducts by the accumulation of mucoid secretions. For example, the invention pertains to methods for treating a subject having a disorder characterized by the obstruction of organ ducts by the accumulation of mucoid secretions, e.g., lung failure occurring in patients afflicted with, e.g., cystic fibrosis. These methods include administering to the subject an agent capable of preventing chondroitin sulfate accumulation such that treatment of the subject occurs.

Depending on the type of organ, the obstruction caused by the accumulation of mucoid secretions, e.g., chondroitin sulfate, is associated with various disorders. For example, the accumulation of mucoid secretions in the lungs can lead to lung failure while the accumulation of mucoid secretions in the gastrointestinal or pancreatic organs can lead to biliary cirrhosis, biliary sludge, gallstones, and common bile duct strictures.

Chondroitin sulfate was identified as the major glucoconjugate secreted by IBE cells by comparing glycoconjugate synthesis and secretion in normal versus CF-IBE cells. IBE-cells were cultured in serum-free medium containing radioactive precursors allowing biochemical analyses of glycoconjugates released into the medium as well as those in cell homogenates. Our results indicate that the major glycoconjugate secreted by IBE cells in chondroitin sulfate and more significantly that the secretion of this proteoglycan is dysregulated in CF-IBE cells compared to cells with normally functioning CFTR.

Various aspects of the invention are described in further detail in the following subsections:

I. Pharmaceutical Compositions

Agents capable of preventing accumulation of a GAG, e.g., chondroitin sulfate, of the invention can be incorporated into pharmaceutical compositions suitable for administration to a subject, e.g., a human. Such compositions typically comprise an enzyme, e.g., chondroitinase, and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a protein capable of degrading chondroitin sulfate) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules encoding agents capable of preventing accumulation of chondroitin can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

II. Uses and Methods of the Invention

The pharmaceutical compositions described herein can be used in one or more of the following methods: a) drug screening assays; b) diagnostic assays; and c) methods of treatment. The pharmaceutical compositions of the invention can thus be used to, for example, prevent accumulation of a GAG, e.g., chondroitin sulfate. The isolated nucleic acid molecules encoding the agents capable of preventing chondroitin sulfate accumulation of the invention can be used to express agents capable of preventing chondroitin sulfate accumulation (e.g., via a recombinant expression vector in a host cell in gene therapy applications), either by degrading chondroitin sulfate or by inhibiting chondroitin sulfate formation as described further below. In addition, the methods described herein can be used to screen drugs or compounds which treat disorders characterized by the accumulation of mucoid secretions.

a. Drug Screening Assays

The invention provides methods for identifying compounds or agents which can be used to treat disorders characterized by (or associated with) by the accumulation of mucoid secretions, e.g., pulmonary and pacreatobiliary disorders, e.g., lung failure, biliary cirrhosis, biliary sludge, gallstones, and common lie duct strictures. These methods are also referred to herein as drug screening assays and typically include the step of screening a candidate/test compound or agent for the ability to prevent accumulation of a GAG, e.g., chondroitin. Candidate/test compounds or agents which have this ability can be used as drugs to treat disorders characterized by the accumulation of mucoid secretions, e.g., pulmonary, gastrointestinal, or pancreatobiliary disorders, e.g., lung failure, biliary cirrhosis, biliary sludge, gallstones, and common bile duct strictures. Candidate/test compounds include, for example, 1) peptides such as soluble peptides, including Ig-tailed fusion peptides and members of random peptide libraries (see, e.g., Lam, K. S. et al. (1991) Nature 354:82–84; Houghten, R. et al. (1991) Nature 354:84–86) and combinatorial chemistry-derived molecular libraries made of D- and/or L- configuration amino acids; 2) phosphopeptides (e.g., members of random and partially degenerate, directed phosphopeptide libraries, see, e.g., Songyang, Z. et al. (1993) Cell 72:767–778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

In one embodiment, the invention provides assays for screening candidate/test compounds which degrade a GAG, e.g., chondroitin. Typically, the assays include the steps of combining a specific amount of chondroitin sulfate and a candidate/test compound, e.g., under conditions which allow for interaction of (e.g., binding of) the candidate/test compound to the chondroitin sulfate. Degradation of the chondroitin sulfate by the candidate/test compound can be quantitated, for example, using optical density analysis.

In another embodiment, the invention provides assays for screening candidates/test compounds which inhibit formation of a GAG, e.g., chondroitin sulfate. Typically, the assays include the steps of combining the candidate/test compound into a system which produces chondroitin sulfate. Inhibition of the formation of chondroitin sulfate by the candidate/test compound can be quantitated by a labeled agent capable of detecting chondroitin sulfate, e.g. $^3$H-glucosamine.

b. Diagnostic Assays

The invention further provides a method for detecting the presence of a disorder characterized by the accumulation of mucoid secretions, e.g., pulmonary, gastrointestinal, or pancreatobiliary disorders, e.g., lung failure, biliary cirrhosis, biliary sludge, gallstones, or common bile strictures in a biological sample. The method involves contacting the biological sample, e.g., sputum sample, with a compound or an agent capable of detecting a GAG, e.g., chondroitin sulfate, determining the amount of chondroitin sulfate expressed in the sample, comparing the amount of chondroitin sulfate expressed in the sample to a control sample, and forming a diagnosis based on the amount of chondroitin sulfate expressed in the sample compared to the control sample. A preferred agent for detecting chondroitin sulfate is a labeled or labelable probe capable of hybridizing to chondroitin sulfate. The probe can be, for example, $^3$H-glucosamine. A preferred agent for detecting chondroitin sulfate is a labeled or labelable antibody capable of binding to chondroitin sulfate. Antibodies can be polyclonal, or more preferably, monoclonal. An intact antibody, or a fragment thereof (e.g., Fab or F(ab')$_2$) can be used. The term "labeled or labelable", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect chondroitin sulfate in a biological sample in vitro as well as in vivo. For example, in vitro techniques for detection of chondroitin sulfate include enzyme linked immunosorbent assays (ELISAs), Western blots, immunoprecipitations and immunofluorescence. Alternatively, chondroitin sulfate can be detected in vivo in a subject by introducing into the subject a labeled anti-chondroitin sulfate antibody. For example, the antibody can be labeled with a radioactive marker whose presence and location in a subject can be detected by standard imaging techniques. The invention further provides a method for monitoring a previously diagnosed subject with a disease characterized by the obstruction of pulmonary, gastrointestinal and pancreatobiliary ducts by the accumulation of mucoid secretions, e.g., pulmonary, gastrointestinal, or pancreatobiliary disorders, e.g., lung failure, biliary cirrhosis, biliary sludge, gallstones, or common bile strictures. The method involves contacting a cell, tissue, or fluid sample, e.g., a sputum sample, from the subject with an agent capable of detecting a GAG, e.g., chondroitin sulfate, determining the amount of chondroitin sulfate expressed in the sample, comparing the amount of chondroitin sulfate expressed in the sample to a the amount of chondroitin sulfate expressed in a sample previously obtained from the same subject to determine the progression of the disease, e.g., measuring the increase or decrease in levels of a GAG, e.g., chondroitin sulfate over time in a subject.

c. Methods of Treatment

Another aspect of the invention pertains to methods for treating a subject, e.g., a human, having a disease or disorder characterized by (or associated with) the accumulation of mucoid secretions. These methods include the step of administering a compound capable of preventing chondroitin sulfate accumulation to the subject such that treatment occurs. Non-limiting examples of disorders or diseases characterized by or associated with the accumulation of mucoid secretions include pulmonary disorders, e.g., lung failure. Examples of disorders or diseases characterized by or associated with the accumulation of mucoid secretions include gastrointestinal and pancreatobiliary disorders, e.g., biliary cirrhosis, biliary sludge, gallstones, and common bile strictures.

The terms "treating" or "treatment", as used herein, refer to reduction or alleviation of at least one adverse effect or symptom of a disorder or disease, e.g., a disorder or disease characterized by or associated with the accumulation of mucoid secretions.

As used herein, a compound capable of preventing chondroitin sulfate accumulation is a molecule which can degrade chondroitin sulfate or inhibit the formation of chondroitin sulfate and thus reduce the symptoms associated with disorders characterized by the accumulation of mucoid secretions. A non-limiting examples of compounds capable of degrading chondroitin sulfate include chondroitinase. A non-limiting example of compounds capable of inhibiting formation of chondroitin sulfate include a nucleic acid.

A subject having a pulmonary disorder can be treated according to the present invention by administering to the subject a compound capable of preventing chondroitin sulfate accumulation such that treatment occurs. Similarly, a subject having a gastrointestinal or pancreatobiliary disorder can be treated according to the present invention by administering to the subject a compound capable of preventing chondroitin sulfate accumulation, such that treatment occurs.

III. Recombinant Expression Vectors and Host Cells

Another aspect of the invention pertains to vectors, preferably expression vectors, containing a nucleic acid encoding a protein that is capable of preventing accumulation of a GAG, e.g., chondroitin sulfate. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for expression of a protein capable of preventing chondroitin sulfate accumulation in prokaryotic or eukaryotic cells. For example, chondroitin sulfate can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, MA) and pRIT5 (Pharmacia, Piscataway, N.J.) which fuse glutathione S-transferase (GST), maltose E binding protein, or protein A, respectively, to the target recombinant protein. In one embodiment, the coding sequence of the chondroitin sulfate is cloned into a pGEX expression vector to create a vector encoding a fusion protein comprising, from the N-terminus to the C-terminus, GST-thrombin cleavage site-chondroitin sulfate. The fusion protein can be purified by affinity chromatography using glutathione-agarose resin. Recombinant chondroitin sulfate unfused to GST can be recovered by cleavage of the fusion protein with thrombin.

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111–2118). Such alteration of nucleic acid sequences of the invention can be carried out by standard DNA synthesis techniques.

In another embodiment, the expression vector is a yeast expression vector. Examples of vectors for expression in yeast *S. cerivisae* include pYepSec1 (Baldari, et al., (1987) *Embo J.* 6:229–234), pMFa (Kurjan and Herskowitz, (1982) *Cell* 30:933–943), pJRY88 (Schultz et al., (1987) *Gene* 54:113–123), and pYES2 (Invitrogen Corporation, San Diego, Calif.).

Alternatively, chondroitin sulfate can be expressed in insect cells using baculovirus expression vectors. Baculovirus vectors available for expression of proteins in cultured insect cells (e.g., Sf9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *PNAS* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to protein capable of degrading chondroitin sulfate mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding chondroitin sulfate or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) chondroitin sulfate protein. Accordingly, the invention further provides methods for producing chondroitin sulfate protein using the host cells of the invention. In one embodiment, the method comprises culturing the host cell of invention (into which a recombinant expression vector encoding chondroitin sulfate has been introduced) in a suitable medium until chondroitin sulfate is produced. In another embodiment, the method further comprises isolating chondroitin sulfate from the medium or the host cell.

While the foregoing discussion has been primarily directed to the detection and treatment of cystic fibrosis, it will be appreciated that the methods of the invention can also be applied to other diseases or conditions in which excess secretion of mucus (which can include mucus which plugs, fills, or otherwise obstructs, or interferes with the functioning of, at least one organ or body lumen) is a symptom or characteristic. For example, chronic otitis media and chronic sinusitis are both characterized by excessive buildup of mucus. Diagnosis and treatment of such conditions with an inhibitor of GAG (e.g., chondroitin sulfate)

synthesis, or a compound capable of degrading a GAG, is possible according to the methods of the invention. Examples of other diseases and conditions which can be diagnosed and/or treated according to the inventive methods include asthma and chronic obstructive pulmonary disease.

The following invention is further illustrated by the following examples, which should not be construed as further limiting. The contents of all references, pending patent applications and published patents, cited throughout this application are hereby expressly incorporated by reference.

EXAMPLES

Example 1
Analysis of Amount and Type of Glycoconjugate

Cell culture: Human intrahepatic biliary epithelial (IBE) cells immortalized by retroviral transduction of SV40 large T antigen were used for the study. Two normal IBE cell lines and two from CF patients, all of which have been characterized previously[13,14] were studied. The normal cells were obtained from disease-free livers that were harvested for transplantation but not used. CF-IBE cells were obtained from CF patients who succumbed to complications due to their airway-associated disease but otherwise had "normal" livers. These epithelial cell lines continued to express in vivo IBE cell markers including cytokeratin 19, gamma glutamyl transpeptidase and ion transporters consistent with biliary function. Genotype analysis of the CF IBE cells has indicated that both patients had the deltaF 508 mutation, that occurs in approximately 70% of the North American CF patient population. Cells were grown in a hormonally supplemented medium (HSM) consisting of Dulbecco's modified Eagle's medium/Nutrient Mixture F-12 Ham (3:1) supplemented with the following: adenine $1.89 \times 10^{-4}$ M, insulin 5 ug/ml, transferrin 5 ug/ml, triiodothyronin $2 \times 10^{-9}$ M, hydrocortisone $1.1 \times 10^{-6}$ M, epinephrine at $5.5 \times 10^{-6}$ M (Intergen Company, Purchase, N.Y., USA) and 10% fetal bovine serum and were maintained at 37° in humidified air and % CO2. Cell culture medium and antibiotics were obtained from Life Technologies (GibcoBRL, Grand Island, N.Y., USA). All other components of the medium were obtained from Sigma Chemical Company (St. Louis, Mo., USA). Cells were plated at a density of approximately 60,000 cells per $cm^2$ and grown to confluence in the presence of serum and growth hormones. Upon reaching confluence, cells were cultured to 16 h in serum-free medium containing luCi/ml $^3$H-glucosamine (GLcN) (New England Nuclear). In some cases $Na_2^{35}SO_4$ or $EXPRE^{35}S^{35}S$ protein labeling mix (DuPont NEN, USA) containing labeled methionine and cysteine was used as a second label. The medium was removed and the cells were washed with an additional volume of label-free medium. The media and washings were pooled and radiolabeled glycoconjugates were precipitated (see below). The cells were collected using a teflon cell-scraper, taken up in 1–2 ml PBS and homogenized by brief sonication. Aliquots of media and cell homogenates were analyzed for the content of radiolabeled glycoconjugates.

In order to eliminate the effect of cell cycle differences which might influence glycoconjugate and synthesis and secretion, cells were synchronized at the start of the study. Upon reaching 80% confluence, cells were subjected to overnight serum deprivation, then cultured in serum-containing medium for 6–8 h. They were then used for secretion studies by culture in serum-free medium containing radioactive precursors as described above.

Trichloroacetic acid/phosphotungstic acid TCA/PTA precipitation: Aliquots of media and cell homogenates were mixed with tCA and PTA to reach a final concentration of 10% TCA and 1% PTA. Precipitates were pelleted by centrifugation, washed extensively for remove unbound radioactive precursors, dissolved in 0.3M NaOH and aliquots taken for scintillation counting. To account for any differences in cell density, aliquots of cell homogenates were assayed for protein by the BCA method[15] and radiolabel incorporation was expressed as DPM per mg of cell protein.

Density gradient ultracentrifugation in cesium chloride (CsCl): Proteins have a buoyant density of 1.3 g/ml versus 1.6 g/ml for carbohydrates. Because of their extensive glycosylation mucins and proteoglycans have a buoyant density (1.5 g/ml) approaching that of carbohydrates. Density gradient ultracentrifugation in cesium chloride is thus a useful technique for their separation. Cesium chloride (45% w/w) was added to dialyzed radiolabeled cell culture media which were than subjected to ultracentrifugation at 100,00 g for 72 h. Fractions of 1 ml were collected by careful aspiration from the top of the tube, and aliquots were used to determine density and radioactivity.

Gel filtration: Radiolabeled culture medium was exhaustively dialyzed against distilled water in the cold to remove unbound label and then subjected to chromatography on a 1.5×12 cm column of Sepharose Cl 4B. One ml samples were loaded and fractions of 0.5 ml collected, aliquots of which were assayed for radioactivity by scintillation counting.

Chemical and enzymatic treatments: Aliquots of media were subjected to beta elimination in 50 mM NaOH/1M $NaBH_4$ at 50° for 48 hours[16] which cleaves )glycosidic linkages, or to digestion by chondroitinase ABC, protease free (E.C.4.2.2.4 from *Proteus vulgaris*) in 250 mM Tris/HCl, 176 mM sodium acetate, 250 mM NaCl, pH 8.0 at 37° for 16 h[17]. Samples incubated under the same conditions without the alkali or enzyme were used as controls. Controls and treated samples were subjected to gel filtration and radioactivity of fractions was determined to monitor any degradation caused by the treatments.

Amino acid analysis[18]: A Perkin Elmer ABI 420A derivatizer was used to determine amino acid compositions. Samples were subjected to automatic hydrolysis in 6N HCl (vapor phase) at 160° C. for 75 min following which amino acids were derivatized with phenylisothiocyanate, separated by HPLC on a ABI 130A Separation System and quantitated by monitoring absorbance at 254 nm.

SDS-PAGE and Western Blot Analysis: Control and chondroitinase digested samples were electrophoresed in 5% polyacrylamide gels according to Laemmli[19], transferred to nitrocellulose membrane by the method of Towbin et al[20]. The nitrocellulose membranes were blocked in 5% dry milk/Tris Buffered Saline/0.05% Tween-20 for 1 h at room temperature and incubated overnight at 4° C. with 1:1000 dilution of primary antibody in 1% milk/TBS/0.05% Tween-20. Primary antibodies tested were rabbit anti-chondroitin sulfate proteoglycan polyclonal antibody (Chemicon International Inc.), monoclonal antibody to MUC-1 tandem repeat (Biogenesis), monoclonal antibody to synthetic human MUC-3 peptide (Biogenesis). After washing the blots were incubated with anti-rabbit or anti-mouse alkaline phosphatase conjugated secondary antibody (Promega, Madison, Wis., USA) diluted 1:7500 in 1% milk/TBS/Tween-20. The blots were washed and developed with nitroblue tetrazolium and bromochloro-indolyl-phosphate.

Figure 1A:
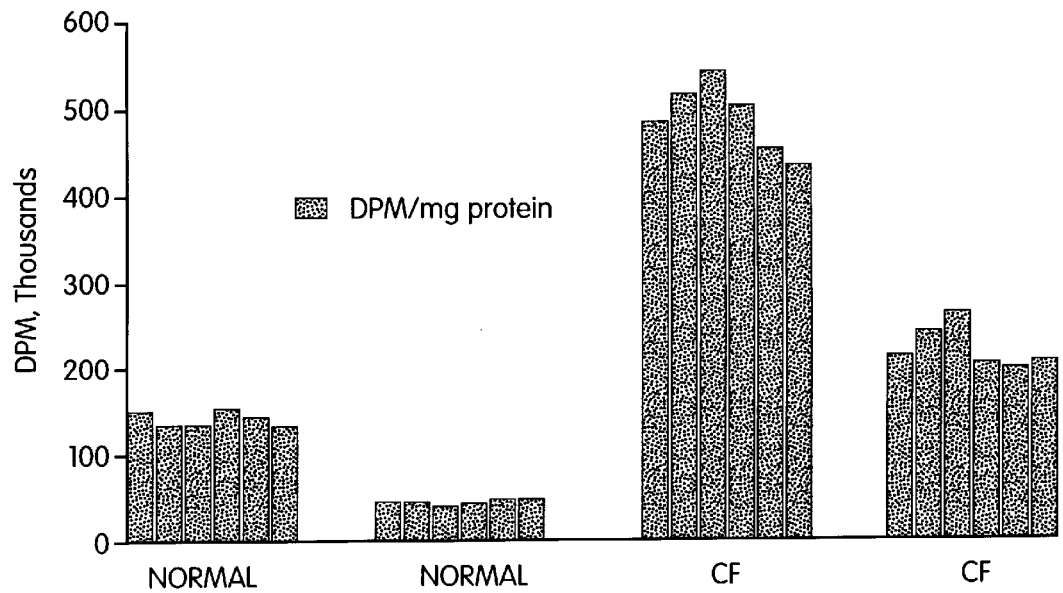
FIG. 1. Incorporation of $^3$H GlcN in TCA/PTA precipitable glycoconjugates from (a) normal and (b) CF IBE cells. Cells from two separate normal and two CF patient lines were plated at the same density in six-well plates and upon reaching confluence were cultured overnight in serum free medium containing 3HGlcN. Medium and cell homogenates were subjected to TCA/PTA precipitation as describe dint the text. Values of the six individual wells are shown for each cell line to demonstrate reproducibility. Incorporation of $^3$H GlcN is markedly higher in the case of CF compared to normal.
Figure 1B:
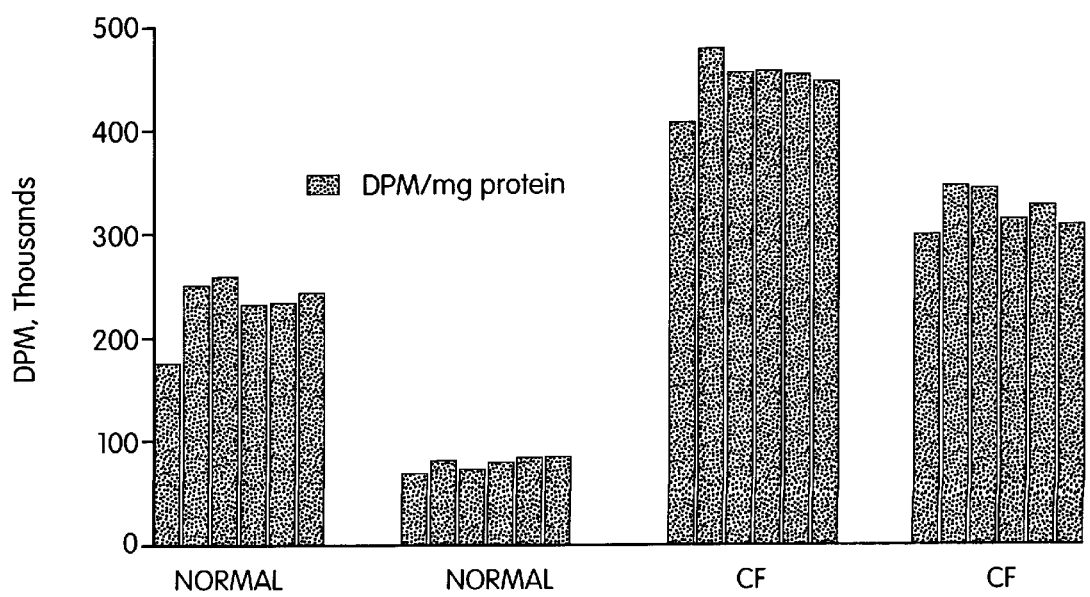

$^3$H-Glucosamine incorporation in TCA/PTA precipitates: After 16 h culture in medium containing $^3$H-GlcN, CF-IBE cells incorporated $^3$HGlcN in TCA/PTA precipitates of medium and cell homogenates at a higher rate than normal IBE cells. Cell lines derived from two different normal or CF patients were studied and both CF cell lines showed higher incorporation compared to the two normals (FIG. 1). Similar results (not shown were observed in experiments where cells were synchronized prior to the secretion studies indicating that the increased incorporation of $^3$H-GlcN by CF cells was not due to cell cycle differences.

Figure 2:
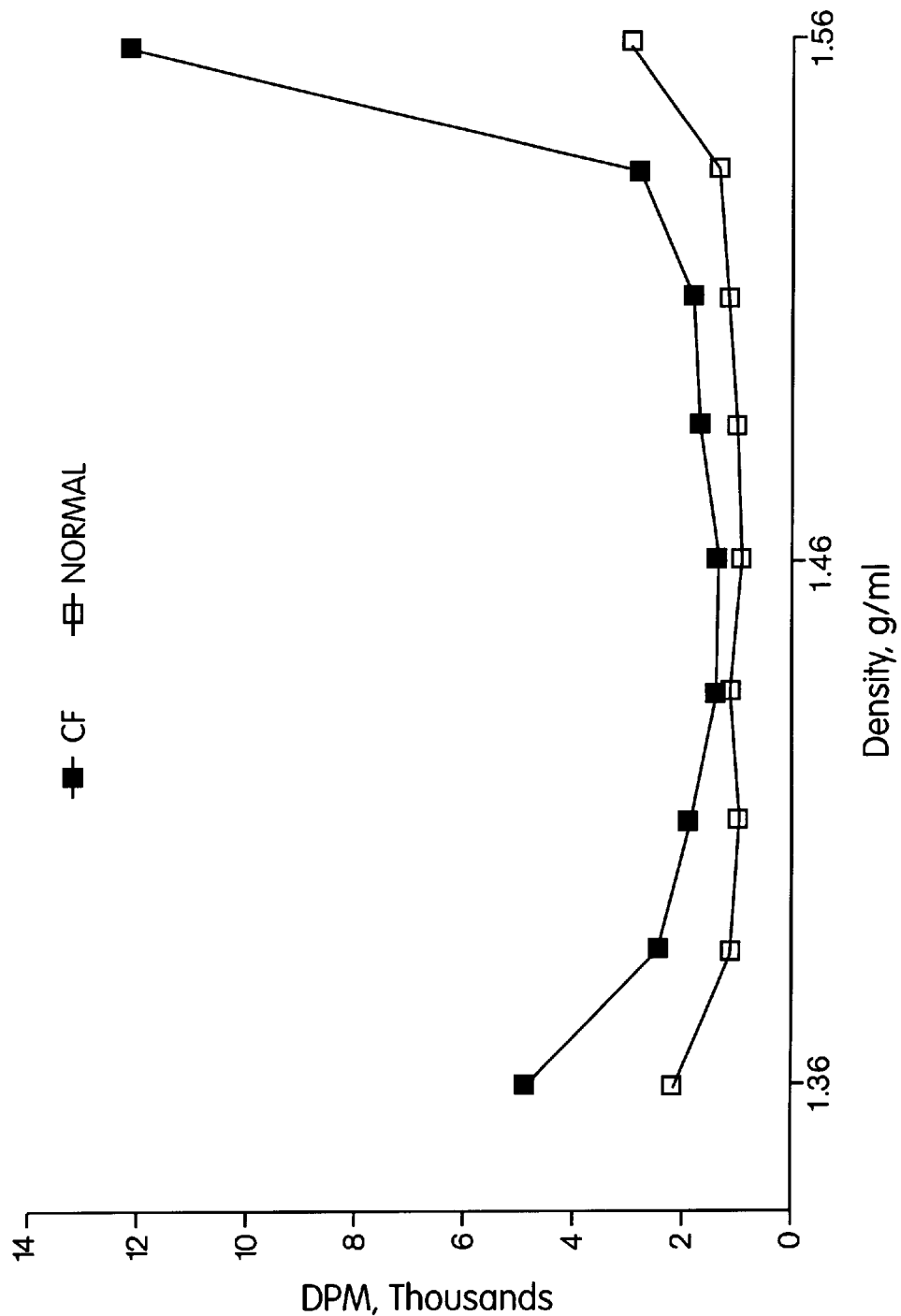
FIG. 2. Density gradient separation of radiolabeled glycoconjugates from IBE cells. Radiolabeled medium from overnight culture of cells was exhaustively dialyzed, lyophilized and subjected to density gradient ultracentrifugation in CsCl as per details in he text. One ml fractions were collected by aspirating from the top and aliquots of reactions were taken for density measurement and scintillation counting. Medium from CF cells has the highest counts in a fraction with density (app. 1.57 g/ml) considerably higher than the buoyant density of mucin (typically 1.5 g/ml). The radioactivity in this fraction is also four-fold higher in CF medium compared to the normal. Both normal and CF medium have significant radioactivity in the low density fractions (1.40 g/ml and lower).

Density gradient ultracentrifugation: The highest incorporation of $^3$HGlcN in the medium from both normal and CF-IBE cells was in fractions of density >1.56 g/ml suggesting incorporation into a highly glycosylated glycoconjugate such as proteoglycan (FIG. 2). Compared to the normal, medium from the CF cells had almost four-fold higher radioactivity in this high density fraction. A minor peak at density 1.36 or lower was also noted.

In order to determine if total protein synthesis was upregulated in CF cells compared to normal, we incubated IBE cells with $^{35}$S methionine as well as $^3$H-glucosamine. As shown in Table 1, incorporation of $^3$H-glucosamine was 40% higher in CF versus normals, while $^{35}$S methionine incorporation was the same in the CF and normal cells. The increase in glucosamine incorporation was even more striking in the high density glycoconjugates.

Gel filtration studies: Medium collected from 16 h culture of IBE cells was subjected to gel filtration on a Sepharose Cl 4B column with an approximate exclusion limit of >2×10$^6$d. Glycoconjugates from CF-IBE cells eluted exclusively in he void volume (see FIG. 3) whereas in medium from normal cells, only 40% of $^3$H-GlcN-labeled macromolecules migrated in the void volume, with the remainder present in a broad peak in the included volume.

Figure 3A:
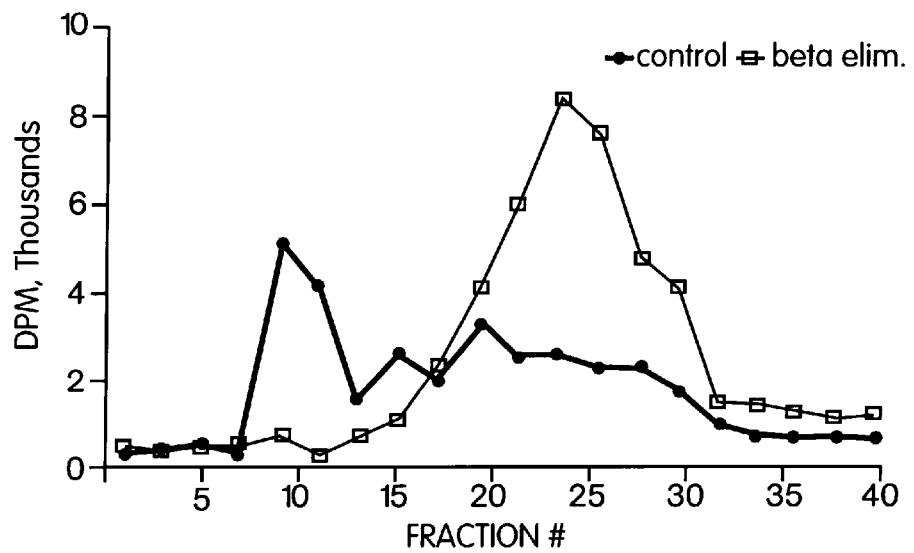
FIG. 3. Susceptibility of glycoconjugates secreted by IBE cells to beta elimination: (a) normal, (b) CF. Non-dialyzable material from overnight culture medium was incubated with alkaline borohydride which cleaves O-linked oligosaccharides and then subjected to gel filtration on Sepharose CL 4B. An aliquot of medium incubated under the same conditions in the presence of buffer alone was used as control. In both normal and CF cell medium, radiolabel in the void volume is completely digested by the treatment indicating that incorporation of radiolabel is primarily in O-linked oligosaccharides. Note that in CF cell medium, incorporation of radiolabel is exclusively in the void volume peak and also that the radioactivity in this peak is markedly higher than in the corresponding peak of the normal cell medium.
Figure 3B:
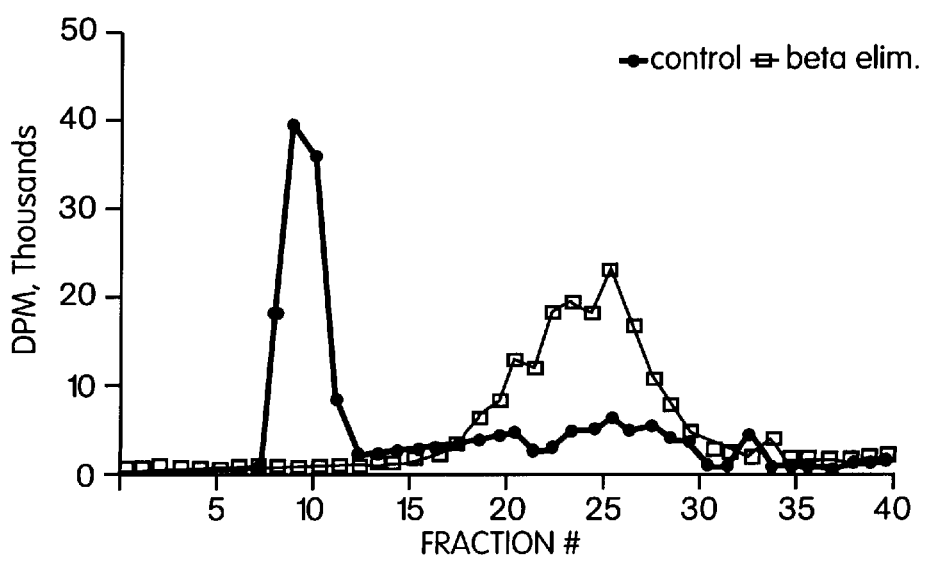
Figure 4A:
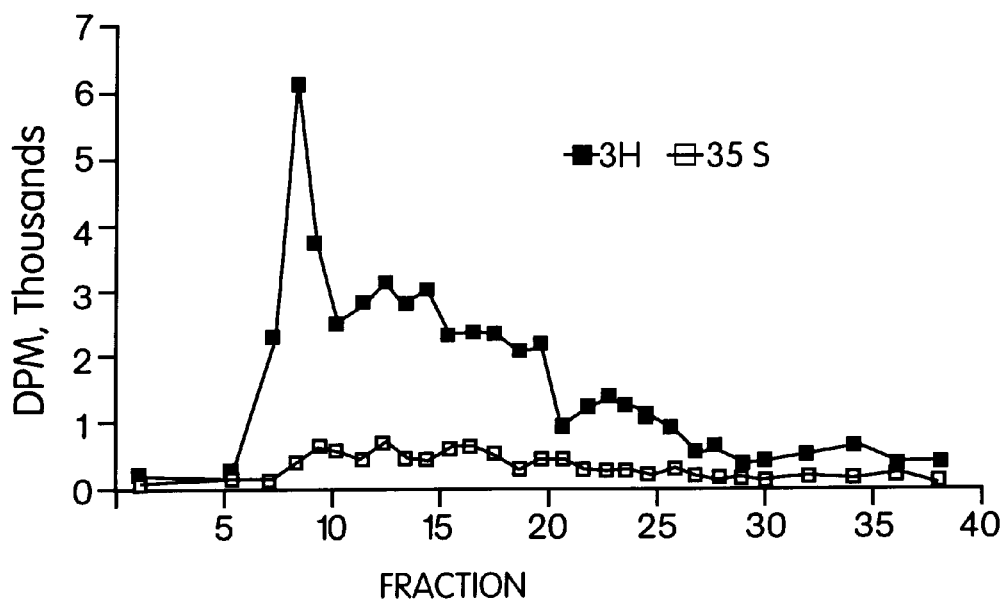
FIG. 4. Chondroitinase digestion of glycoconjugates secreted by normal and CF IBE cells. Non-dialyzable radiolabelled ($^3$H GlcN and $^{35}$S Na$_2$SO4) glycoconjugates from culture medium were incubated with chondroitinase ABC and subjected to gel filtration on Sepharose CL4B. Medium incubated with buffer alone under the same conditions was used as control. In control medium from CF cells (b), both labels were confined to a narrow peak in the void volume but after enzyme digestion both labels were found in a broad peak in the included volume (d), indicating that chondroitin sulfate is the predominant labeled glycoconjugate in the CF cell medium. Chondroitin sulfate is also a major secretory product of the normal cell but enzyme digestion of the medium is not as complete as in the case of CF cell medium suggesting the presence of other O-linked glycoconjugates, possibly mucin(?).
Figure 4B:
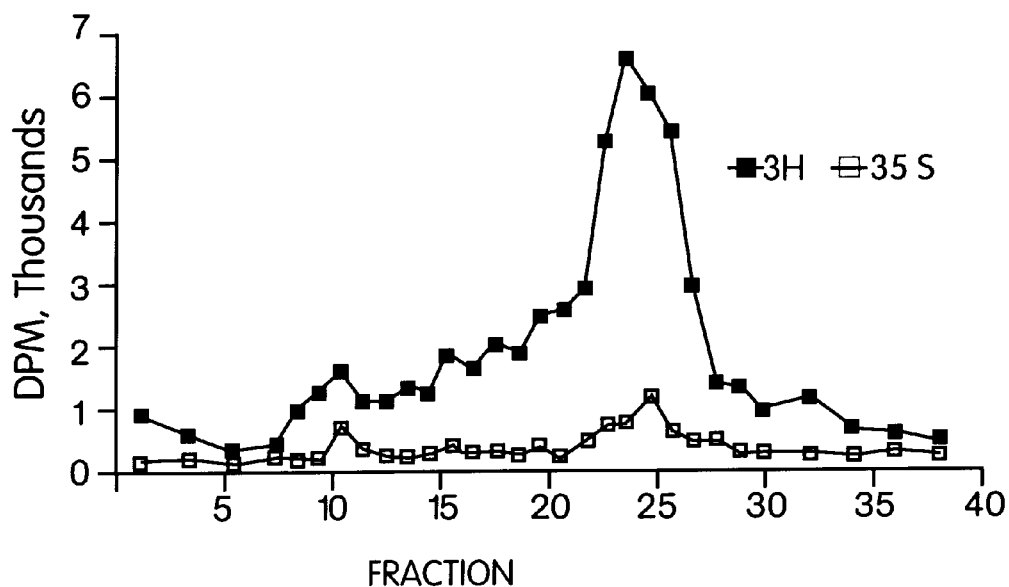
Figure 4C:
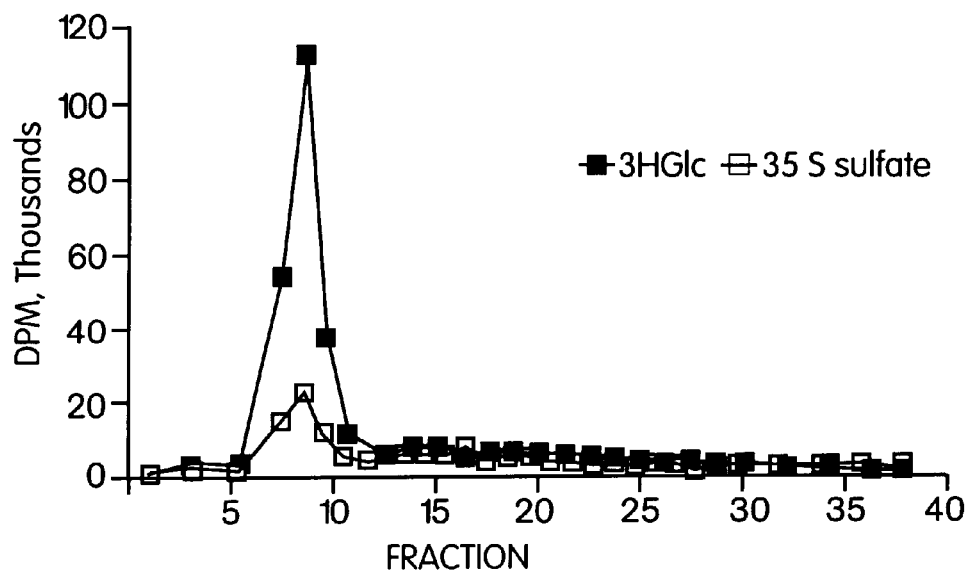
Figure 4D:
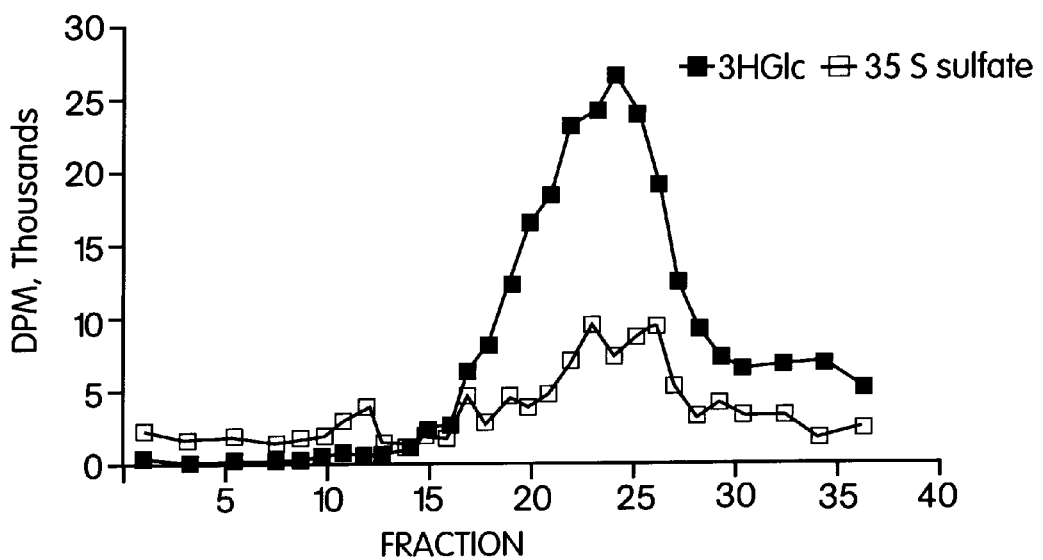

Chemical and enzymatic treatments of secreted glycoconjugates: The oligosaccharide chains in mucins are attached to serine and threonine residues via O-glycosidic linkages that are sensitive to cleavage with alkaline borohydride. After such cleavage, radiolabeled glycoconjugates in medium from both normal an dCF-IBE cells were found only in the included fractions and not in the void volume indicating that all the $^3$H GlcN was incorporated into O-linked oligosaccharides (FIG. 3).

Since proteoglycans also have a high buoyant density and their oligosaccharide chains are susceptible to cleavage by alkaline borohydride, we treated secreted glycoconjugates from both normal and CF-IBE cells with chondroitinase ABC followed by gel filtration. IBE cells were labeled with both radioactive glucosamine ($^3$H GlcN) and sulfate ($^{35}$SO4) in this experiment (FIG. 4). In the undigested medium from CF-IBE cells, $^3$H GlcN or $^{35}$S-glycoconjugates were confined to a narrow peak in the void volume (4b) whereas after chondroitinase digestion these glycoconjugates eluted in a broad peak in the included volume (4d). This indicates that the high density glycoconjugate (FIG. 2) secreted by CF-IBE cells is predominantly chondroitin sulfate. The high density fraction from normal IBE cell medium (FIG. 4A) was also degraded by the enzyme (FIG. 4C) although some label remained in the void volume peak suggesting the presence of other glycoconjugates in addition to chondroitin sulfate.

Amino acid composition of the secreted high density glycoconjugates fractions from one normal and two CF-IBE cell lines are shown in Table I. Noticeably absent are the high ratios of Ser and Thr typical of mucins; rather Ser, Gly and Glx are the most predominant ones, as expected for proteoglycans. Search of a protein composition database using Propsearch[21] indicated that human and rat cartilage-specific proteoglycan (CSPG) core protein resembled the composition determined for glycoconjugates secreted by IBE cells (Table I). Some of the differences seen in Table I are to be expected since the composition of CSPG is based on sequence data, unlike that of the biliary cell glycoconjugates. The content of GLY is considerably higher in the IBE cell glycoconjugates compared to that in CSPG. Since all three IBE cell glycoconjugates have comparable levels of Gly, it is unlikely that this results from contamination but is more likely due to expected differences between secreted and cartilage proteoglycans.

Figure 5:
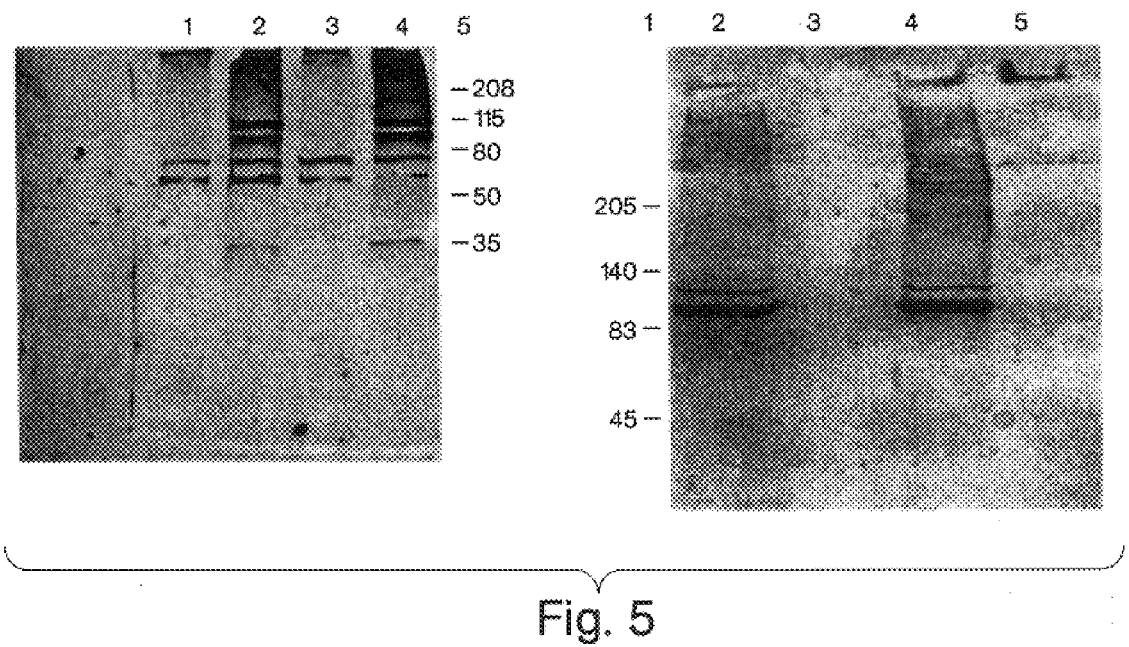
FIG. 5. Western Blot analysis of glycoconjugates secreted by biliary cells using anti-chondroitin sulfate proteoglycan antibody a) Void volume fractions of the secreted glycoconjugate were digested with chondroitinase ABC, separated by 4–15% SDS-Page, transferred to nitrocellulose and examined for reactivity to a polyclonal antibody to chondroitin sulfate. Lanes 1, 2, undigested and enzyme-digested normal IBE medium 3,4, undigested and enzyme-digested CF-IBE medium, 5 molecular weight markers. Undigeted medium from both normal and CF cell medium show very weakly reactive bands at approximately 70 kD and 80 kD. These bands are also seen in the digested medium form both cell types, but much stronger bands are seen in the enzyme digested medium at approximately 90 kD, 115 kD and three closely-spaced bands >208 kD. The markedly higher intensity of the bands at 90 kD and those >208 kD in the CF cell medium (lane 4) compared to the normal (lane 2) suggests increased amounts of chondroitin sulfate in CF cell medium, b) low density (<1,45 g/ml) fractions examined in %5 SDS-PAGE as in (a) above: lane 1, molecular weight markers, 2, 2, enzyme-digested and undigested normal IBE cell medium 4,5,enzyme-digested and undigested CF-IBE cell medium. A positively stained band is seen at app. 90 kd, the markedly higher intensity of the band in CF cell medium suggesting higher amounts of chondroitin sulfate.
Figure 6A:
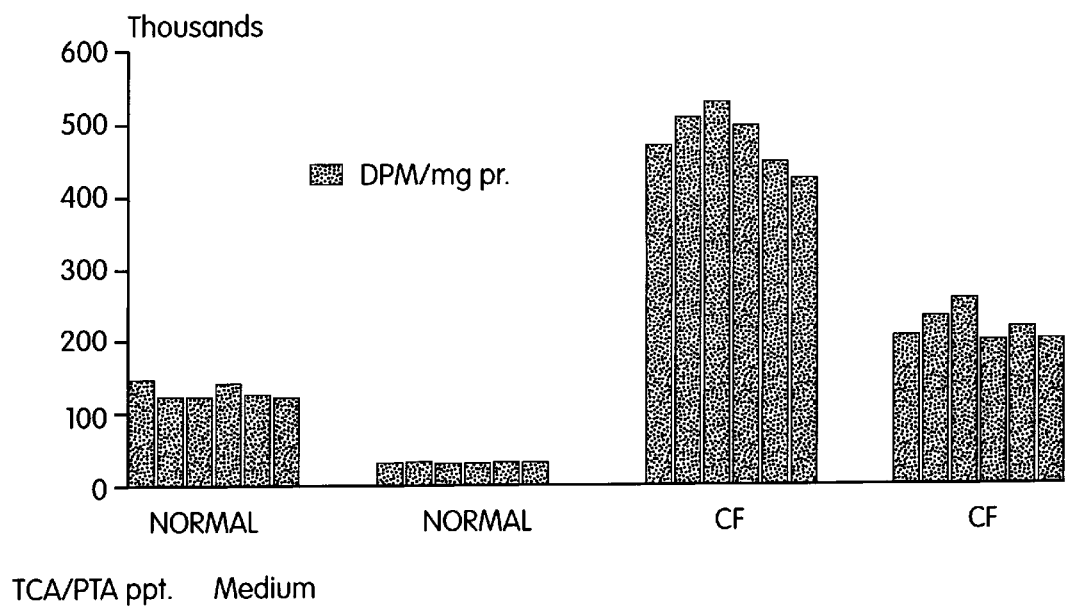
FIG. 6. Incorporation of $^3$H glucosamine in TCA/PTA precipitable glycoconjugates is markedly higher in both medium (top panel) and cell homogenates (bottom panel) of CF biliary cells compared to normal.
Figure 6B:
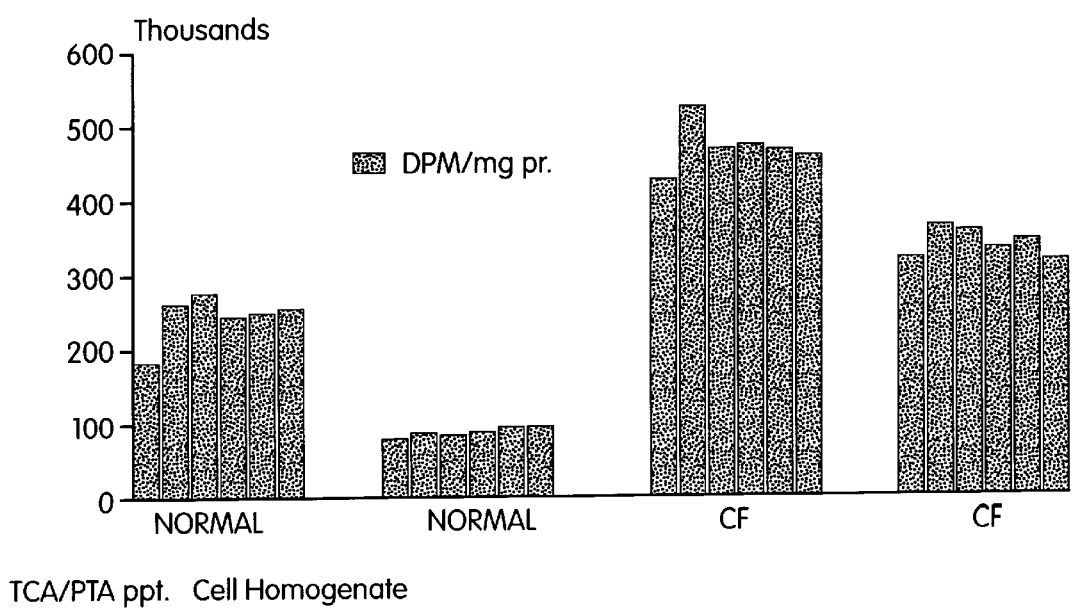

To confirm the present of chondroitin sulfate in the IBE cell medium, Western blot analysis was carried out using a polyclonal antibody against chondroitin sulfate proteoglycan that recognizes antigens present on the sulfated GlcU-GaINAc disaccharide that are detectable only after chondroitinase ABC digestion[22]. SDS-PAGE followed by Western blot analysis showed the presence reactive proteins at larger than 208, 115 and 90 kD in medium from both normal (FIG. 5a, lane 2) and CF cells (FIG. 5a, lane 4) which were not seen in the undigested sample (FIG. 5a, lanes 1 and 3). The most prominent of these, at 90 kd, was also seen in he low density (<1.45 g/ml) fraction (FIG. 5b). The intensity of staining of the >208 kd bands (FIG. 5a, lanes 4 versus 2) and the band at 90 kd (FIG. 5b, lanes 4 versus 2) was higher in he medium from CF compared to normal IBE cells. The increased intensity of the 90 id band is particularly striking in the low density fraction (FIG. 5b, lane 4 compared to lane 2). For each cell line, medium from the same number of wells of equal cell density was used in his experiment and therefore the greater intensity of the bands further confirms that CF cells secrete higher amounts of chondroitin sulfate.

Recent studies have suggested the presence of MCU-1 and MUC-3 proteins in human bile[23,24]. Dot and Western blot analysis of medium from CF and normal IBE cells did not show any reactivity to monoclonal antibodies capable of detecting human MCU-1 or MUC-3 peptides.

The major finding of our study was that IBE cell lines from two different CF patients exhibited increased incorporation of $^3$H-glucosamine into high molecular weight proteoglycans compared to cells derived from two normals. Neither the CF nor the normal IBE cells were derived from patients with clinical or histological evidence of liver disease thus we think it is unlikely that antemortem pathologic changes would influence our results. The immortalized CF-IBE cell lines used in our study have been characterized previously as lacking a functional CFTR as evidenced by the lack of response to forskolin/IBMX in the SPQ halide efflux assay[14]. The normal biliary epithelial cells immortalized under similar conditions, provide a reliable control for our studies and it is reasonable to infer that the observed differences between normal and CF-IBE cells are due to the defective CFTR.

How can defect in a cAMP regulated chloride channel affect epithelial glycoconjugate secretion? While the mechanism for such a linkage is currently not know, evidence for a direct association between mutated CFTR and mucus hypersecretion is provided by observations in mice with targeted disruptions of the murine CFTR gene[25,26]. Homozygous mutant mice (CFTR−/−) showed goblet cell hyperplasia of the intestine and died of intestinal obstruction due to accumulation of putty-like material containing mucus. It has been suggested that decreased chloride transport in CF would alter the pH in intracellular organelles which in turn could affect the activities of glycosyltransferases, enzymes that attach monosaccharides to secreted glycoproteins[27]. This could lead to qualitative and/or quantitative changes of mucin and other secreted glycoconjugates. Recent studies by Bradbury et al[28] showed that epithelial cells from a CF patient lacked cAMP dependent regulation of endocytosis and exocytosis which was restored after transfection of the cells with cDNA encoding wild-type cFTR. This observation suggests that secretion of mucin which occurs through compound exocytosis could be dysregulated in the absence of a normally functioning CFTR. Another hypothesis is that decreased chloride permeability in CF cells might result in a compensatory increase in the intracellular pool of glucose or sulfate that might in turn alter the sulfation or glycosylation of glycoconjugates[29]. Secretory granules of CF cells appear to have elevated sulfur content and cell and organ culture studies have shown increased sulfation in CF compared to normal[30, 31]. Kuver et al[32] reported that overexpression of CFTR increased mucin secretion in gallbladder epithelial cells. Insertion of a normal CFTR has been shown to correct the defective beta-adrenergic regulation of mucin and chloride secretion of CF cells. In our studies, the relatively higher incorporation of $^3$H-glucosamine in CF IBE cell medium compared to normal suggests increased glycosyltransferase activity but further studies are needed to establish which of the above factor(s) is responsible for our observations.

A second important observation in our study was that the major glycoconjugate secreted by CF and normal IBE cells was not mucin, but chondroitin sulfate. This identification was based on three independent criteria vis., susceptibility to digestion by chondroitinase ABC, amino acid composition and reactivity to anti-chondroitin sulfate antibody. Although mucin is often considered to be the major glycoconjugate secreted by epithelial cells, recent studies have documented that proteoglycans are also secreted by epithelial cells in culture[29,33,34]. Chondroitin sulfate is a major connective tissue proteoglycan and is not usually considered to be a component of epithelial secretions. However, this molecule and other proteoglycans have been identified in sputum[35,36].

Based on our observations, we speculate that upregulation of proteoglycan secretion by CF IBE cells bearing defective CFTR may be a factor in CF associated liver disease. One of the early histologic changes found in children with CF is blockage of bile ductules with inspissated secretions. The frequent occurrence of bile duct plugging with granular eosinophilic material not unlike the inspissated material blocking the pancreatic ducts in CF suggests that abnormalities of glycoconjugate secretion are common in the proximal biliary tree of CF patients. Although the inspissated eosinophilic material in CF bile ducts is often assumed to be "mucus", biochemical characterization has not been reported. We speculate that excessive secretion and accumulation of proteoglycans by IBE cells as described here could contribute to the formation of biliary plugs. Highly charged anionic polymers like chondroitin sulfate could polymerize at high concentrations leading to the formation of eosinophilic mucus plugs. Alternatively, anionic glycosaminoglycans could interact with mucin molecules to form complex polymers of high viscosity[37].

The relevance of our observations to the pathobiology of CF may extend beyond the biliary tract. Bovine tracheal serous cells have recently been shown to synthesize and secrete a chondroitin sulfate proteoglycan in vitro[38]. Since serous cells in the lung express the CFTR, by analogy with our findings with CF-IBE cells, serous cells of CF patients bearing mutated CFTR might secrete increase amounts of proteoglycans. Interestingly, Rahmoune et al[35] have recently reported the presence of chondroitin sulfate in sputum from CF patients. Although the authors associated the presence of chondroitin sulfate to the state of infection, our studies and those of Brahimi-Horn et al[38] suggest that secretion of chondroitin sulfate can occur independently of infection. It is possible that such secretion can facilitate survival of *P. aeruginosa*, the capsular polysaccharide of which has constituents similar to proteoglycans. This may also explain the observation that *P. aeruginosa* has usually been found in microcolonies in airway mucus of CF patients rather than attached to epithelial cells.

Table 1. $^3$H GlcN and $^{35}$S Methionine Incorporation into Glycoconjugates Secreted by IBE Cells.

Cells (one normal and one CF) were plated in 4×100 mm dishes and cultured as described in the text. Values given are per dish. Medium from all four dishes of each line was pooled, subjected to density gradient ultracentrifugation and the radiolabel incorporation in the high density (>1.45 g/ml) glycoconjugate fraction is shown in the bottom row*.

| Normal | | CF | |
|---|---|---|---|
| 3H | 35$_S$ | 3$_H$ | 35$_S$ |
| 2615 | 21062 | 3793 | 23772 |
| 2768 | 21497 | 3444 | 21585 |
| 2495 | 20293 | 3762 | 21507 |
| 2873 | 21879 | 3967 | 22628 |
| *3848 | 4826 | 6286 | 4679 |

TABLE 2

Amino Acid Composition of Glycoconjugates Secreted by IBE Cells (Expressed as residues/1000 residues)

| Amino Acid | Normal | CF-1 | CF-2 | CSPG |
|---|---|---|---|---|
| Asp | 77 | 58 | 72 | 57 |
| Glx | 155 | 112 | 123 | 136 |
| Ser | 131 | 125 | 93 | 123 |
| Thr | 36 | 38 | 38 | 82 |
| Gly | 342 | 381 | 295 | 121 |
| Ala | 64 | 44 | 67 | 69 |
| Pro | 36 | 44 | 67 | 69 |
| Val | 31 | 33 | 50 | 77 |
| Met | 0 | 11 | 12 | 0 |
| Ileu | 21 | 21 | 34 | 34 |
| Leu | 32 | 33 | 50 | 77 |
| His | 12 | 0 | 9 | 14 |
| Tyr | 12 | 12 | 18 | 20 |
| Phe | 11 | 48 | 22 | 28 |
| Lys | 27 | 26 | 39 | 12 |
| Arg | 13 | 15 | 29 | 33 |

Radiolabeled void volume material was subjected to density gradient ultracentrifugation in CsCl and the high density fraction was used for the analysis; CF-1 and CF-2 are from two different CF-IBE cell lines. Composition for cartilage specific proteoglycan (CSPG) core protein is based on published sequence data and is included here for comparison.

Example 2

Effect of Chondroitinase ABC on the Solubility of CF Sputum

MATERIALS:

Buffer: 0.2M Tris-HCl pH 7.4 containing 0.2M Sodium acetate.

Enzymes used in the study were as follows:

Chondroitinase ABC (Chondroitin ABC lyase: EC 4.2.2.4) from *proteus vulgaris* was obtained from Sigma Chemical Co. Chondroitinase ABC was dissolved in the above buffer at a concentration of 1U/100 μl.

Hyaluronidase from Streptomyces Hyaluronlyticus was obtained from CalBiochem and was dissolved in the same buffer at a concentration of 100U/$\mu$l.

Human recombinant DNAse (trade name Pulmozyme) was obtained from the Wellesley Hospital, Toronto, Ontario. Pulmozyme was supplied as a 1 mg/ml solution in 0.15M Sodium Chloride.

All the 3 enzymes were stored at $-20°$ C. after each use.

Fresh sputum was collected from adult CF out patients and immediately stored at $-20°$ C. With the adult CF in patients the sputum was collected over a period of 4–6 hours and then stored at $-20°$ C. The amount and consistency of sputum varied from patient to patient. In most cases, the sputum was quite thick and thus processing of the sputum samples proved to be quite a challenge. In some cases the sputum was yellow or reddish yellow in color.

ABBREVIATIONS: ChABC, Chondroitinase ABC; hyalu, Nyaluronidase; Pulmo, Pulmozyme

METHODS

Sputum samples were dispersed by gentle pipeting several times (5–10 times, depending on its thickness) through a large mouth plastic pipette. Duplicate aliquots (~0.5 ml) of CF sputum from each patient were incubated with or without chondroitinase ABC/Hyaluronidase/Pulmozyme in the present of 0.75–1 ml Tris buffer pH 7.4 containing Sodium acetate. All incubations were carried out at 37° C. for 18 h with shaking. Chondroitinase ABC was used at a concentration of 1U/reaction; Hyaluronidase was used at a concentration of 1U/reaction; and Pulmozyme was used at a concentration of 10 $\mu$g/reaction unless stated otherwise. At the end of incubation the samples were centrifuged at 12000 rpm for 20 min at 4° C. In each case turbidity of the supernatant was measured by spectroscopy (O.D 600) and any change in the pellet size (gel phase) was also recorded. In most cases the tubes following centrifugation were photographed.

Experiments were carried out to optimize the time and speed of centrifugation and to study the effect of buffer alone if any on CF sputum solubility.

In order to optimize the time and speed of centrifugation for measurement of the el phase, CF sputum samples (~0.5 ml) with or without buffer were centrifuged at the following speed and time intervals: 2,500 rpm for 30 min; 12,000 rpm for 5, 10 and 20 min. At the end of each centrifugation the size of the pellet was measured.

Observations: The pellet size essentially remained the same in each case. Thus, in all further experiments, centrifugation was carried out at 12,000 rpm for 20 mins at 4° C. as it was convenient to do so in the laboratory.

The effect of buffer alone on CF sputum solubility was studied. Buffer chosen for this study was 0.2M Tris-Hcl pH 7.4 containing Sodium acetate. Six similar aliquots (~0.5 ml each) of sputum from Patient #4 was mixed with 0.9 ml buffer. The samples were centrifuged for 20 mins at 12,000 rpm and O.D 600 readings measured for each supernatant. The same samples were then incubated at 37° C. for 18 h with shaking. At the end of incubation the tubes were centrifuged once again at 12,000 rpm and O.D 600 readings were obtained for each supernatant.

The results are presented below:

| Supernatant (#) | O.D. 600 (Before incubation) | O.D. 600 (After 18 h incubation) |
|---|---|---|
| 1 | 0.052 | 1.540 |
| 2 | 0.032 | 1.250 |
| 3 | 0.048 | 0.791 |
| 4 | 0.026 | 1.038 |
| 5 | 0.036 | 0.972 |
| 6 | 0.024 | 0.895 |

Observations:

Incubation of CF sputum for 18 h at 37° C. with shaking in the presence of buffer alone caused a dramatic increase in the turbidity of the supernatant. the increase in turbidity may likely be a result of sputum breakdown due to shearing. The presence of salt may have further assisted in releasing components from the sputum gel contributing to increased turbidity. Thus, in determining the effect of different enzymes on the solubility of CF sputum, a duplicate control sample of sputum incubated in the presence of buffer alone was used in each case.

The effect of Chondroitinase ABC on the sputum of CF Patient #4 was studied and compared to that of Pulmozyme. Method:

Sputum samples in duplicate were treated with or without Chondroitinase ABC/Pulmozyme in the presence of Tris buffer. Incubations were carried out in the presence of either 1U Chondroitinase ABC, or 10 ug Pulmozyme essentially as described earlier. The changes in supernatant were measured by O.D. 600 readings and the size of each pellet was recorded as well.

The results of the experiment are shown below. The supernatants are numbered in pairs and represent duplicate sputum samples.

| Supernatant | | O.D.600 (turbidity) | % drop (turbidity) | Pellet size in mm (Low) | (High) |
|---|---|---|---|---|---|
| | Chondroitinase | | | | |
| 1 | None | 0.908 | — | 9 mm | 11 mm |
| 1 | 1 U | 0.192 | 78.8% | 6 mm | 9 mm |
| 2 | None | 0.907 | — | 11 mm | 14 mm |
| 2 | 1 U | 0.173 | 80.9% | 5 mm | 8 mm |
| | Pulmozyme | | | | |
| 1 | None | 1.972 | | 10 mm | 14 mm |
| 1 | 10 ug | 0.550 | 72% | 6 mm | 9 mm |
| 2 | None | 1.805 | | 11 mm | 14 mm |
| 2 | 10 ug | 0.462 | 74% | 6 mm | 11 mm |

Observations: Treatment of sputum with Chondroitinase ABC caused a dramatic drop in the turbidity of supernatant. This was accompanied by a significant drop in the pellet size following the enzyme treatment.

The effect of Pulmozyme on the sputum supernatant and pellet was essentially the same i.e. a drop in supernatant turbidity and a reduction in pellet size.

The optimum concentration under the conditions of this particular experiment of Chondroitinase ABC was determined. Method: Increasing concentrations of Chondroitinase ABC were incubated with the same amount of sputum. At each concentration of the enzyme, a duplicate sample of sputum with buffer alone served as a control. The incubation and centrifugation steps were carried out essentially as described earlier.

The results of the experiment are shown below. The supernatants are numbered in pairs and represent duplicate sputum samples.

| Supernatant | Chondroitinase concentration | O.D.600 | % drop (turbidity) | Pellet size in mm (Low) | Pellet size in mm (High) |
|---|---|---|---|---|---|
| 1 | None | 1.540 | — | 10 mm | 15 mm |
| 1 | 0.01 U | 0.698 | 54.6% | 10 mm | 12 mm |
| 2 | None | 1.250 | — | 11 mm | 15 mm |
| 2 | 0.1 U | 0.484 | 61.2% | 8 mm | 9 mm |
| 3 | None | 0.791 | — | 11 mm | 13 mm |
| 3 | 0.25 U | 0.251 | 68.2% | 6 mm | 10 mm |
| 4 | None | 1.038 | — | 10 mm | 12 mm |
| 4 | 0.5 U | 0.129 | 87.5% | 5 mm | 9 mm |

Observations: The results clearly indicate that Chondroitinase ABC at concentration as low as 0.1U per reaction is able to cause a dramatic drop both in supernatant turbidity as well as pellet size. In subsequent experiments Chondroitinase was used at concentration of 1U per reaction i.e. under conditions of excess enzyme.

The effect of chondroitinase ABC on the solubility of sputum collected from 6 different CF patients was studied to determine if Pulmozyme causes a similar effect on CF sputum.

Duplicate aliquots (~0.5 ml) of sputum from each patient were incubated with or without 1U chondroitinase ABC in the presence of Tris buffer. The incubation and centrifugation steps were carried out essentially as described earlier. The results of this experiment are as follows:

| Patient # | Enzyme | O.D.600 (supernatant) | % drop (turbidity) | Pellet size in mm (Low) | Pellet size in mm (High) |
|---|---|---|---|---|---|
| 4 | None | 0.820 | | 12 mm | 12 mm |
| 4 | None | 0.834 | | 12 mm | 12 mm |
| | | (Mean 0.827) | | | |
| 4 | 1 U ChABC | 0.083 | 89.9% | 4 mm | 8 mm |
| 4 | 1 U ChABC | 0.078 | 90.5% | 4 mm | 7.5 mm |
| 4 | Pulmo (10 ug) | 0.068 | 91.7% | 4 mm | 8 mm |
| 4 | Pulmo (20 ug) | 0.080 | 90.3% | 4 mm | 8 mm |
| 4 | Trypsin (6 U) | 1.135 | Increase | 7 mm | 9 mm |
| 6 | None | 0.886 | — | 10 mm | 12 mm |
| 6 | None | 0.825 | | 10 mm | 12 mm |
| | | (Mean 0.855) | | | |
| 6 | 1 U ChABC | 0.070 | 91.81% | 4 mm | 8 mm |
| 6 | 1 U ChABC | 0.068 | 92.04% | 4 mm | 8 mm |
| 6 | Pulmo (10 ug) | 0.084 | 90.17% | 4 mm | 8 mm |
| 6 | Pulmo (20 ug) | 0.078 | 90.8% | 4 mm | 8 mm |
| 6 | Trypsin (6 U) | 0.583 | 31.8% | 5 mm | 8 mm |
| 6 | Trypsin (6 U) | 0.447 | 47.7% | 5 mm | 8 mm |
| 5 | None | 0.294 | — | 10 mm | 12 mm |
| 5 | 1 U ChABC | 0.092 | 68.7% | 9 mm | 11 mm |
| 5 | Pulmo (10 ug) | 0.109 | 62.9% | 9 mm | 11 mm |
| 2 | None | 0.060 | — | 4 mm | 7 mm |
| 2 | 1 U ChABC | 0.036 | 40% | 1 mm | 3 mm |
| 2 | Pulmo (10 ug) | 0.038 | 36.6% | 1 mm | 3 mm |
| 3 | None | 0.055 | — | pellets very small | |
| 3 | 1 U ChABC | 0.028 | 49% | | |
| 3 | Pulmo (10 ug) | 0.028 | 49% | | |
| 1 | None | 0.020 | — | pellets very small | |
| 1 | 1 U ChABC | 0.004 | 80% | | |
| 1 | Pulmo (10 ug) | 0.006 | 70% | | |

Observations: Incubation of sputum from 6 different CF patients essentially showed the same results i.e. reduction in supernatant turbidity accompanied by a significant reduction in pellet size except for CF Patient #5. It is important to note that the effect of Chondroitinase ABC on CF sputum has been very consistent throughout this entire study.

The effect of ChABC were compared with that of Pulmozyme and Trypsin. The results obtained using Pulmozyne were essentially the same as ChABC. The effect of Trypsin was studied on 2 patients (#4 and #6). In one patient, Trypsin caused an increase in supernatant turbidity, whereas in other a reduction in turbidity. The pellet sizes in both cases were reduced.

Sputum from 2 patients (Patient #6 and 37) were used in this experiment. Sputum samples in duplicates from each patient were incubated with/without Chondroitinase ABC (1U) and Hyaluronidase (2U) respectively. In parallel, sputum samples in duplicate were also incubated with 10 µg DNase (from bovine pancreas). The reactions were carried out at 37° C., for O/N with shaking. At the end of the incubation, tubes were centrifuged at 4° C. for 20 mins at 12,000 rpm. The turbidity of the supernatants were measured by O.D 600 and the pellet size in each case was estimated by visual inspection. The results of this experiment are as follows:

| Patient # | Enzyme | O.D.600 | % drop in O.D | % drop in pellet size |
|---|---|---|---|---|
| 6 | None | 0.341 | — | 50% |
| 6 | ChABC + Hyalu | 0.158 | 53% | |
| 6 | None | 0.509 | — | |
| 6 | DNase | 0.273 | 46% | 20% |
| 7 | None | 0.125 | — | |
| 7 | ChABC + Hyalu | 0.083 | 34% | 40% |
| 7 | None | 0.193 | | |
| 7 | DNase | 0.095 | 51% | 50% |

Observations: This early experiment carried out on CF sputum using the two enzymes Chondroitinase ABC and Hyaluronidase together indicated a reduction in the turbidity of the supernatant accompanied by a reduction in pellet size. The effect of DNase was essentially the same as that of Chondroitinase ABC and Hyaluronidase.

In this experiment a control sample of CF sputum as used previously served as the starting material. This control sample of sputum had already gone through an O/N incubation at 37° C. in the presence of buffer alone in the previous experiment. Equal aliquots (~100 µl each) of this sample was used to study the effects of 3 different enzymes added individually or in combination. The reactions were carried out in a total volume of 0.5 ml at 37° C. essentially as described earlier. The results of the supernatant turbidity following each treatment were measured and are summarized as follows:

| Enzyme | O.D. 600 (supernatant) | % drop in turbidity |
|---|---|---|
| No enzyme | 0.512 | — |
| Chondroitinase ABC (0.2 U) | 0.208 | 59% |
| Hyaluronidase (0.5 U) | 0.194 | 62% |
| Pulmozyme (5 ug) | 0.228 | 55% |
| Chondroitinase ABC + Hyaluronidase + Pulmozyme | 0.209 | 605 |

Observations:

All 3 enzymes tested caused a reduction in supernatant turbidity in the range of 55–62%. The effect of 3 enzymes added together was about the same (60%) and thus not additive. There as a significant drop in pellet size following ChABC or Pulmozyme treatment. However, the pellet size did not change following Hyaluronidase treatment. Thus, the effect of Hyaluronidase on gel phase of CF sputum was distinct from that of ChABC.

The effect of Hyaluronidase alone on the solubility of CF sputum (Patient #4) was studied. Increasing concentration of hyaluronidase (0.1U, 0.5U and 2U) were incubated with the same amount of sputum from Patient #4. At each concentration of enzyme, a duplicate sample of sputum with buffer alone served as a control. Incubation was carried out at 37° C. for O/N with rotary shaking. The results of this experiment are as follows:

| Super-natant | Hyaluronidase concentration | O.D 600 (supernatant) | % drop (turbidity) | Pellet size in mm (Low) | (High) |
|---|---|---|---|---|---|
| 1 | None | 0.972 | — | 17 mm | 20 mm |
| 1 | 0.1 U | 0.340 | 54.6% | 16 mm | 20 mm |
| 2 | None | 0.895 | — | 14 mm | 17 mm |
| 2 | 0.5 U | 0.285 | 61.2% | 15 mm | 18 mm |
| 3 | None | 0.494 | — | 9 mm | 15 mm |
| 3 | 2 U | 0.148 | 68.2% | 11 mm | 16 mm |

Observations:

The results clearly indicate that Hyaluronidase at concentration as low as 0.1U caused a dramatic drop in supernatant turbidity. However, unlike Chondroitinase treatment, this drop was not accompanied by a reduction in pellet size. In fact, the pellet showed a slight increase in size following Hyaluronidase treatment. Thus, the effect of Hyaluronidase on CF sputum solubility is quite distinct from that of chondroitinase ABC.

This experiment was carried out using samples of sputum from a previous experiment. These samples had already been treated either with Chondroitinase ABC or Hyaluronidase. These enzyme treated sputum samples thus served as a starting material in the following study:

Sputum samples (that had been previously treated with Chondroitinase ABC) were subjected to an O/N incubation with/without Chondroitinase ABC at 37° C. with shaking. At the end of incubation, samples were centrifuged and O.D 600 readings were obtained for supernatant and pellet size was measured in each case. The results of the experiment are as follows:

| | Chondroitinase treated samples (O.D 600 of supernatant) | Chondroitinase treatment followed by Hyaluronidase (O.D 600 of supernatant) |
|---|---|---|
| 1 | 0.698 | 0.739 |
| 2 | 0.484 | 0.560 |
| 3 | 0.251 | 0.224 |
| 4 | 0.129 | 0.153 |

Observations:

Incubation of Chondroitinase treated sputum samples with Hyaluronidase did not cause a significant change in supernatant turbidity. Furthermore, the pellets remained essentially the same in size.

| Hyaluronidase treated samples | | | Hyaluroindase treatment follows by Chondroitinase ABC | | |
|---|---|---|---|---|---|
| (Supernatant) | Pellet Size | | (Supernatant) | Pellet Size | |
| O.D 600 | Low | High | O.D 600 | Low | High |
| 1 | 15 mm | 20 mm | 0.908 | 9 mm | 10 mm |
| 2 | 15 mm | 18 mm | 0.678 | 7 mm | 8 mm |

Observations:

Incubation of Hyaluronidase treated samples with chondroitinase ABC caused a significant increase in supernatant turbidity. This is in contrast to the effect of Chondroitinase ABC, when used alone. However, there appeared to be a significant drop in pellet size, a feature of Chondroitinase treatment.

Cystic Fibrosis (CF) is the most common autosomal recessive disorder among the Caucasian population worldwide with the incidence of heterozygous carriers estimated at 1 in 2000. On of the key clinical problems in CF is the blockage of certain organs by thick mucus secretions. This may occur in the lung, bile ducts, pancreas and intestinal tract, with resulting damage to the organ involved. Recently the genetic defect in CF has been identified to be in the regulation of chloride ion transport across cell membranes. This finding explains the increased sweat chloride concentration of CF patients and provides a scientific basis for this standard diagnostic test for CF. However, it is still not clear how this genetic defect in the chloride ion transport regulator leads to mucus obstruction. Transgenic mice bearing the defective (CFTR, cystic fibrosis transmembrane regulator) gene have been found to suffer from intestinal mucus obstruction confirming that there is a direct link between the two.

The component primarily responsible for the viscous properties of mucus is mucin, a large polymeric glycoprotein secreted by the epithelial cells. The focus in the study of pathobiology of CF is therefore to determine whether mucus obstruction in CF arises from abnormalities in the quantity and/or quality of secreted mucin. For our studies we have used biliary tract cells which are known to express CFTR, the gene that is defective in CF patients. These cells are immortalized to grow continuously in the laboratory thus allowing us to carry out repeated studies to systematically determine the rates and nature of secretions released by the cells. WE have immortalized biliary cells from CF patients which bear the defective CFTR gene as well as cells from normals with properly functioning CFTR. Using radioactive tracers, we have analyzed the glycoprotein secretions from two normal and two CF biliary cell lines.

The above studies have thus shown both qualitative and quantitative abnormalities of mucus secretion by CF biliary cells. Although mucin has been considered to be the major glycoconjugate of mucus, secretion of proteoglycans by airway epithelial cells has been demonstrated by our previous studies as well as studies from other researchers. To our knowledge, this is the first study describing the nature of glycoconjugates secreted by biliary epithelial cells. Since obstruction of biliary ducts in CF affect 20–30% of CF patients, this new information on the nature of the secretion might lead to new approaches for therapy.

We have some preliminary evidence that our observations of increased secretion of polymeric glycoconjugates may apply to other cells bearing defective CFTR. tissue culture studies using mouse intestinal tissue from wild type mice and knockout mice without CFTR (CFTR −/−) mice have shown similar effects.

It is possible that our findings may have relevance to pulmonary pathology which is the most severe and clinically important in CF. Previous studies with expectorated sputum have not revealed any striking abnormalities of mucin in CF patients compared to other hypersecretory diseases like asthma or chronic bronchitis. This partly, if not entirely, due to the presence of infection and inflammation at the time of onset of sputum production by a CF patient. It is conceivable that an early effect of the abnormal gene is similar to that observed by us with biliary cells, namely increased secretion of proteoglycans. In the lungs, the serous cells which are thought to provide baseline secretion, are known to secrete proteoglycans and these are the cells that bear CFTR, the gene that is defective in CF. If our observations with CF biliary cells apply t he defective CFTR in the serous cells would result in increased production of proteoglycans and this might be the basis for the repeated infection with Pseudomonas. This might then set off the secondary chain of inflammation and hypersecretion by mucous cells which secrete typical mucin. Our findings could lead to early intervention in the lung which might prevent the secondary effects of infection and inflammation.

In the course of our studies, some differences, qualitative as well as quantitative, between the glycoconjugates secreted by normal and CF biliary cells were found.

Incorporation of the radioactive precursor $^3$H glucosamine in the precipitate obtained from the medium and cell homogenates using the reagent trichloroacetic acid/ phosphotungstic acid (TCA/PTA) was observed. Precipitation with this reagent is routinely used as an index of glycoconjugate secretion and it was clear that this was markedly higher in the case of CF cells compared to the normal.

Gel filtration patterns of the medium on a Sepharose Cl 4B column also were observed. Medium from cell culture was dialyzed to remove unbound label before gel filtration and fractions were analyzed for radioactivity. Large polymeric molecules are not retained by the column and thus appear first in this fractionation. It was seen that radioactive incorporation was almost exclusively in a large polymeric species in the case of CF cell medium, whereas in the normal the radioactivity was distributed over a broad peak with considerable material of smaller size. The large size of the $^3$H labeled macromolecules secreted by CF cells was likely to result in solutions of higher viscosity.

To determine if the labeled macromolecules were mucins or proteoglycans, culture medium from biliary tract cells was incubated with the enzyme chondroitinase ABC, which digests away chondroitin sulfate and reexamined by gel filtration.

The gel filtration patterns of medium before and after such treatment was observed. Surprisingly, medium from the CF cells was completely digested by the enzyme, the radiolable after the treatment being found in the smaller (included fractions, indicating that the glycoconjugate secreted by the CF IBE is predominantly chondroitin sulfate. Medium from the normal cells was also digested by the enzyme but not completely. This was further confirmed by the observation that enzyme digested medium reacted positively to a commercially obtained polyclonal antibody to chondroitin sulfate.

Equivalents

Those skilled in the art will recognize, or be able to ascertain using no more than routine experimentation, numerous equivalents to the specific procedures described herein. Such equivalents are considered to be within the scope of this invention and are covered by the following claims.

The contents of all publications, issued patents, pending patent applications, and published patent applications cited herein are hereby incorporated by reference.

Other embodiments are within the following claims.

References

1. Boat T., Welsh M. J. and Beaudet A. Cystic Fibrosis In: Scriver C. et al. eds., *The Metabolic Basis of Inherited Disease*. 6th ed. New York, McGraw-Hill, 2649–2680, 1989.
2. Anderson, M., Gregory R. J., Thompson S., et al. Demonstration that CFTR is a chloride channel by alteration of its anion selectivity. *Science* 253:202–205, 1991.
3. Tizzano, E. F. and Buchwald M. CFTR expression and organ damage in cystic fibrosis. *Ann Int. Med* 123:305–308, 1995.
4. Tizzano, E. F. and Buchwald M. Cystic fibrosis: beyond the gene to therapy. *J. Pediatr.* 120:337–349, 1992.
5. Welsh, M. J., Anderson M. P., Rich D. P. et al. Cystic fibrosis transmembrane conductance regulator: a chloride channel with novel regulation. *Neuron* 8:821–829, 1992.
6. Welsh, M. J. and Smith A. E. Molecular mechanisms of CFTR chloride channel dysfunction in cystic fibrosis. *Cell* 73:1251–1254, 1993.
7. Cheng S. H., Gregory R. J., Marshall J., et al. Defective intracellular transport and processing of CFTR is the molecular basis of most cystic fibrosis. *Cell* 63:827–834, 1990.
8. Zabner J., Peterson D. M., Puga A. P. et al. Safety and efficacy of repetitive adenovirus-mediated transfer of CFTR cDNA to airway eoithelia of primates and cotton rats. *Nature Genetics* 6:75–83, 1984.
9. Lopez M. J., Grand R. J. Hereditary and childhood disorders of the pancreas. In: *Gastrointestinal Disease: Pathophysiology/Diagnosis/Management*. Sleisenger M. H. and Fordtran J. S. eds. Philadelphia, Saunders, p. 1601–1627, 1993.
10. Yang Y., Raper S. E., Cohn J. A. et al. An approach for treating the hepatobiliary disease of cystic fibrosis by somatic gene transfer. *Proc. Natl. Acad. Sci. USA* 90:4601–4605, 1993.
11. Ghisham F. K. and Greene H. L. Inborn errors of metabolism that lead to permanent liver injury. In: *Hepatology, A Textbook of Liver Diseases*. Zakim D and Boyer T. D., eds. Saunders p. 1124, 1982.
12. Cohn J. A., Strong T. V., Picciotto M. R. et al. Localization of the cystic fibrosis transmembrane conductance regulator in human bile duct epithelia cells. *Gastroenterology* 105:1857–1864, 1993.
13. Grubman S. A., Perrone R. D., Lee D. W. et al. Regulation of pH by immortalized human intrahepatic biliary epithelial cell lines. *Am. J. Physiol.* 266:G1060–G1070, 1994.
14. Grubman S. A., Fang S. L., Mulberg A. E. et al. CFTR gene complementation in intrahepatic biliary epithelial cell lines derived from patients with cystic fibrosis. *Gastroenterology* 108:584–592, 1995.
15. Smith P. K., Krohn R. I. Hermanson G. T., et al. Measurement of protein using bicinchoninic acid. *Anal. Biochem. Biophys.* 42:101–105, 1971.
16. Iyer R. N. and Carlson D. J. Alkaline borohydride degradation of blood group H substance. *Arch Biochem. Biophys.* 42:101–105, 1971.

17. Oike Y., Kimata K., Shimomura T. et al. Structural analysis of chick embryo cartilage proteoglycan by selective degradation with chondroitin lyases (chondroitinases) and endo-beta-D-galactosidase (keratanase). *Biochem. J.* 191:193–207, 1980.
18. Moore S. and Stein W. H. Chromatographic determination of amino acids by the use of automatic recording equipment. *Methods Enzymol.* 6:819–831, 1963.
19. Laemmli, U. K. Cleavage of structural proteins during the assembly of the head of bacterophage T4. *Nature* 227:680–685, 1970.
20. Towbin H., Staehelin T. and Gordon J. Electrophoretic transfer of proteins from polyacrylamide gels to nitrocellulose sheets: Procedures and some applications. *Proc. Natl. Acad. Sci.* 76:4350–4354, 1979.
21. Hobohm U., Houthaeve T. and Sander C. Amino acid analysis and protein database composition search as a fast and inexpensive method to identify proteins. *Anal. Biochem* 222:202, 1994.
22. Bertolotto A., Palmucci L., Gagliano A., et al. Immunohistochemical localization of chondroitin sulfate in normal and pathological human muscle. *J. Neurol. Sci.* 73:233–244, 1986.
23. Baekstron D., Karlsson N. and Hansson G. C. Purification and characterization of sialyl-Le(a)-carryin(g mucins of human bile: evidence for the presence of MUC1 and MUC3 apoproteins. *J. Biol. Chem.* 269:14430–437, 1994.
24. Sasaki M., Nakanuma Y., Terada T., Kim Y. S. Biliary epithelial expression of MUC1, MUC2, MUC3 and MUC5/6 apomucinsduring intrahepatic bile duct development and maturation. An immunohistochemical study *Am. J. Pathol.* 147(3):574–579, 1995.
25. Snouwaert J. N., Brigman K. K., Latour A. M. et al. An animal model for cystic fibrosis made by gene targeting. *Science* 257:1083–1088, 1992.
26. Ratcliff, R., Evans M. J., Cuthbert A. W., et al. Production of a severe cystic fibrosis mutation in mice by gene targeting. *Nature Genetics* 4:35–41, 1993.
27. Barasch J., Kiss A., Prince L. Defective acidification of intracellular organelles in cystic fibrosis. *Nature* 352:70–73, 1991.
28. Bradbury N. A., Jilling T., Berta G. Regulation of plasma membrane recycling by CFTR. *Science* 256:530–532, 1992.
29. Cheng P-W, Boat T. F., Cranfill K., et al. Increased sulfation of glycoconjugates by cultured nasal epithelial cells from patients with cystic fibrosis. *J. Clin. Inves.* 84:68–72, 1989.
30. Izutsu K., Johnson D., Schubert M. et al. Electron microprobe analysis of human labial gland secretory granules in cystic fibrosis. *J. Clin. Invest.* 75:1951–56, 1985.
31. Zhang, Y., Doranz J. R., Yankaskas J. R. and Engelhardt J. F. Genotypic analysis of respiratory mucous suflation defects in cystic fibrosis. *J. Clin Inves.* 96:2997–3004, 1995.
32. Kuver, R., Ramesh N., Lau, S. et al. Constitutive mucin secretion linked to CFTR expression. *Biochem. Biophys. Res. Comm.* 203:1457–1462, 1994.
33. Bhaskar K. R., O'Sullivan D. D., Opaskar-Hineman H. et al. Density gradient analysis of secretions produced in vitro by human and canine airway mucosa: identification of lipids and proteoglycans in such secretions. *Exp. Lung Res.* 10:401–422, 1986.
34. Kim K. C., Hineman H. O., Bhaskar K. R. Secretions from primary hamster tracheal epithelial cells in culture: Mucin, proteoglycans and lipids. *Exp. Lung. Res.* 15:299–314, 1989.
35. Rahmoune H., Lamblin G., Lafitte J. J., et al. Chondroitin sulfate in sputum from patients with cystic fibrosis and chronic bronchitis. *Am. J. Respir. Cell. Mol. Biol.* 5:315–320, 1991.
36. Bhaskar K. R., Brown R., O'Sullivan D. D. et al. Bronchial mucus hypersecretion in acute quadriplegia: macromolecular yields and glycoconjugate composition. *Am. Rev. Respir. Dis.* 143:640–648, 1991.
37. Foster S. N. E., Pearson J. P., Hutoon D. A., et al. Interaction of polyacrylates with porcine pepsin and the gastric mucus barrier: a mechanism for mucosal protection. *Clin. Sci.* 87:719–726, 1994.
38. Brahimi-Horn M. D., Deudon E., Paul A., et al. Identification of decorin proteoglycan in bovine tracheal serous cells in culture and localization of decorin mRNA in situ. *Eur. J. Cell Biol.* 64:271–280, 1994.

What is claimed is:

1. A method for treating a subject having a disorder characterized by the accumulation of mucoid secretions, comprising administering to the subject a therapeutically effective amount of an agent that prevents chondroitin sulfate accumulation such that treatment of the subject occurs, wherein the agent is a chondroitinase enzyme.

2. The method of claim 1, wherein the agent prevents chondroitin sulfate accumulation by degrading the chondroitin sulfate.

3. The method of claim 2, wherein the disorder is a pulmonary disorder.

4. The method of claim 3, wherein the pulmonary disorder is cystic fibrosis.

5. The method of claim 2, wherein the disorder is a pancreatobiliary disorder.

6. The method of claim 5, wherein the pancreatobiliary disorder is biliary cirrhosis.

* * * * *